US007544666B2

(12) United States Patent
Lee et al.

(10) Patent No.: US 7,544,666 B2
(45) Date of Patent: Jun. 9, 2009

(54) NAP DERIVATIVES

(75) Inventors: On Lee, Hsinchu (TW); Jenn-Tsang Hwang, Hsinchu (TW); Chrong-Shiong Hwang, Hsinchu (TW); Yuan-Jang Tsai, Hsinchu County (TW); Chen-Yi Su, Hsinchu (TW); Tsan-Lin Hu, Pingtung County (TW); Shing Mein Wu, Hsinchu (TW); Chiu Hsing Lin, Pingtung County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 11/440,174

(22) Filed: May 25, 2006

(65) Prior Publication Data

US 2007/0142269 A1 Jun. 21, 2007

(30) Foreign Application Priority Data

Dec. 20, 2005 (TW) .............................. 94145293 A

(51) Int. Cl.
*A61K 38/00* (2006.01)
*A61K 38/04* (2006.01)
*A61K 38/08* (2006.01)
*C07K 7/00* (2006.01)

(52) U.S. Cl. .............................. 514/15; 514/2; 514/16; 530/300; 530/328

(58) Field of Classification Search ....................... None
See application file for complete search history.

(56) References Cited

U.S. PATENT DOCUMENTS

| | | | | |
|---|---|---|---|---|
| 4,966,848 A | * | 10/1990 | Smith et al. | 435/193 |
| 5,223,421 A | * | 6/1993 | Smith et al. | 435/193 |
| 5,767,240 A | | 6/1998 | Brenneman et al. | |
| 5,837,218 A | * | 11/1998 | Peers et al. | 424/1.69 |
| 6,174,862 B1 | | 1/2001 | Brenneman | |
| 6,613,740 B1 | | 9/2003 | Gozes et al. | |
| 6,933,277 B2 | | 8/2005 | Brenneman et al. | |
| 2002/0028763 A1 | | 3/2002 | Shade et al. | |
| 2002/0111301 A1 | | 8/2002 | Brenneman et al. | |
| 2004/0048801 A1 | | 3/2004 | Spong et al. | |
| 2004/0053313 A1 | | 3/2004 | Gozes et al. | |

OTHER PUBLICATIONS

Dementia (Alzheimer's Disease) from the Merck manual.*
Parkinsons's disease from the Merck manual.*
Brenneman et al., The Journal of Pharmacology and Experimental Therapeutics, 2004, pp. 1190-1197, vol. 309, No. 3.
Zaltzman et al., Neuropharmacology and Neurotoxicology, Mar. 2003, pp. 481-484, vol. 14, No. 3.
Alcalay et al., Neuroscience Letters, 2004, pp. 128-131, 361.
Ashur-Fabian et al., Peptides 24, 2003, pp. 1413-1423.
Beni-Adani et al., The Journal of Pharmacology and Experimental Therapeutics, 2001, pp. 57-63, vol. 296, No. 1.
Blondel et al, The Journal of Neuroscience, Nov. 1, 2000, pp. 8012-8020, 20(21).
Brenneman et al., Biochemical Society Transactions, 2000, pp. 452-455, vol. 28, part 4.
Dicinski et al, The Journal of Biological Chemistry, Jul. 2, 2004, pp. 28531-28538, vol. 279, No. 27.
Furman et al., Neuron Glia Biology, 2005, pp. 1-7, 1.
Gozes et al., Annals New York Academy of Sciences, pp. 115-118.
Gozes et al, Journal of Alzheimer's Disease 6, 2004, pp. 37-41.
Gozes et al., Journal of Molecular Neuroscience, 2000, pp. 61-68, vol. 14.
Gozes et al., Journal of Molecular Neuroscience, 2003, pp. 315-322, vol. 20.
Gozes et al. Journal of Molecular Neuroscience, 2004, pp. 67-72, vol. 24.
Sari et al. Brain Research Reviews, 2006, pp. 1-12, 4C.
Gozes et al, The Journal of Pharmacology and Experimental Therapeutics, pp. 1091-1098, vol. 293, No. 3.
Gozes et al., Trends in Neurosciences, Dec. 2001, pp. 687-690, 700-705, vol. 24, No. 12.
Lagrèze et al., Investigative Ophthalmology & Visual Science, Mar. 2005, pp. 933-938, vol. 46, No. 3.
Leker et al., Stroke, Apr. 2002, pp. 1085-1092.
Pinhasov et al., Developmental Brain Research, 2003, pp. 83-90, vol. 144.
Poggi et al., Department of Obstetrics and Gynecology, Oct. 2002, pp. 973-976, vol. 187, No. 4.
Poggi et al., Department of Obstetrics and Gynecology, Sep. 2003, pp. 790-793, vol. 189, No. 3.
Romano et al., Journal of Molecular Science, 2002, pp. 37-45, vol. 18.
Spong et al., The Journal of Pharmacology and Experimental Therapeutics, 2001, pp. 774-779, vol. 297, No. 2.

(Continued)

*Primary Examiner*—Cecilia Tsang
*Assistant Examiner*—Julie Ha
(74) *Attorney, Agent, or Firm*—Birch, Stewart, Kolasch & Birch, LLP

(57) ABSTRACT

An oligopeptide comprises formulae (I) or (II)

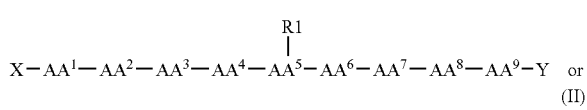

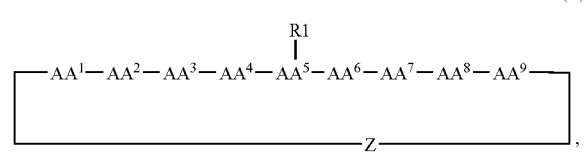

the oligopeptide derivative thereof, and a pharmaceutical composition comprising the same are provided.

12 Claims, 15 Drawing Sheets

OTHER PUBLICATIONS

Steingart et al., Journal of Molecular Neuroscience, 2000, pp. 137-145, vol. 15.

Visochek et al., The Journal of Neuroscience, Aug. 10, 2005, pp. 7420-7428, 25(32).

Wilkemeyer et al, The Journal of Pharmacology and Experimental Therapeutics, 2004, pp. 1183-1189, vol. 309, No. 3.

Wilkemeyer et al., PNAS, Jul. 8, 2003, pp. 8543-8548, vol. 100, No. 14.

Zaltzman et al., Peptides 26, 2005, pp. 1520-1527.

Zamostiano et al., The Journal of Biological Chemistry, Jan. 5, 2001, pp. 708-714, vol. 276, No. 1.

Zemlyak et al., Peptides 96, 2000, pp. 39-43.

Zusev et al., Peptides 123, 2004, pp. 33-41.

\* cited by examiner

NAP DERIVATIVES

BACKGROUND OF THE INVENTION

1. Field of the Invention

The present invention relates to oligopeptide derivatives for neural protection, regeneration, and repair.

2. Description of the Related Art

Alzheimer's disease (AD) is named after Dr. Alois Alzheimer, a German doctor. In 1906, Dr. Alzheimer noticed changes in the brain tissue of a woman who had died of an unusual mental illness. He found abnormal clumps (now called amyloid plaques) and tangled bundles of fibers (now called neurofibrillary tangles). Today, these plaques and tangles in the brain are considered signs of AD. AD patients may have symptoms such as forgetfulness, slovenliness, anxiety, aggressiveness, or cognitive impairment. Eventually, patients suffer from AD need complete care from friends, relatives, or care-givers. The symptoms of AD in the early stage may be confused with age-related physiological and psychological changes and accurate laboratory diagnostic method for AD is still unavailable, making diagnoses and control of AD difficult. Pathological changes of AD include, not only senile plaques with β-amyloid deposits and neurofibrillary tangles in the cerebral cortex, but also loss of cholinergic neurons in the basal forebrain and decrease of acetylcholine and choline acetyltransferase in the cerebral cortex.

Recent studies show that nerve growth factors (NGF) and brain-derived neurotrophic factor (BDNF) apparently enhance the growth and differentiation of embryonic cholinergic neurons in vitro. The application of NGF or BDNF to the lateral ventricle or brain parenchyma can protect cholinergic neurons of basal forebrain from degeneration caused by dissection of hippocampus and thus alleviate the severity of dementia. Besides nerve growth factors and brain-derived neurotrophic factor, known neurotrophic factors also include glial cell-derived neurotrophic factor (GDNF), neurotrophin 3 (NT-3), vasoactive intestinal peptide (VIP), NAP, activity-dependent neurotrophic factors (ADNFs), and activity-dependent neurotrophic protein (ADNP).

ADNP and ADNFs were first isolated from glial cells by Dr. Brenneman (National Institute of Health) in collaboration with Dr. Gozes (Tel Aviv University) during the study of VIP. ADNP and ADNFs both are ultra potent neurotrophic factors with activities around femtomolar level. ADNF-14 (VLGGGSALLRSIPA) (SEQ ID NO: 1) derived therefrom has stronger activity than ADNP. Follow-up studies of Brenneman and Gozes reveal that ADNF-9. (SALLRSIPA) (SEQ ID NO: 2) and NAP (NAPVSIPQ) (SEQ ID NO: 3) both derived from ADNF are also femtomolar-acting neurotrophic factors.

In vitro experiments found that ADNF-14, ANDF-9 and NAP can protect neural cells from degeneration or death caused by GP120 of HIV, NMDA (an excitatory toxin), dopamine, 6-hydroxydopamine, ferrous sulfate, hydrogen peroxide, β-amyloid (an inferential neuron toxin of Alzheimer's disease), tetrodotoxin (a sodium channel blocker), and presenilin-1. In in vivo experiments, ADNF-14, ADNF-9 and NAP also showed neuroprotective activities in cerebral palsy mouse and apolipoprotein E knock-out mouse and prevented choline-deficient mouse from loss of the abilities of spatial learning and memorization. In addition, a long term protection (about 5 days) may be achieved by a short term (2 hours) exposure to these peptides. The various neuroprotective and neurotrophic effects of these peptides indicate that they may act at the very basic steps of molecular biology for cells to survive.

The discovery of ADNF-14, ADNF-9 and NAP established a new concept of designing femtomolar-active and long-acting oligopeptides derived from high molecular weight proteins. These peptides can be leads for the development of drugs to alleviate, postpone, or prevent the onset of Alzheimer's disease and also for the treatment of Parkinson's disease, cerebral vascular disease, or the regeneration of neurons.

Though ADNF-14, ADNF-9, and NAP are potential candidates for drug development, they also have the same drawbacks as common peptide drugs. For example, peptides may be degraded by proteases and lose their activities; the configuration thereof with a higher degree of freedom might lower their affinities and selectivity toward receptors, hinder the drugs to penetrate cell membrane or blood brain barrier, and exhibit multiple mechanisms of action that make the concentration-activity relationships thereof do not follow a simple sigmoid curve. One purpose of this invention is overcoming the described drawbacks to provide a novel neurotrophic drug with excellent stability, good absorption, long half-life, and superior drug exposure for the treatment of Alzheimer's disease, Parkinson's disease, stroke, or cognitive impairment resulting from neural intoxication, neural injury, spinal injury, or coronary artery bypass surgery.

BRIEF SUMMARY OF THE INVENTION

To improve the stability, absorption, half-life, and exposure of NAP, a series of novel NAP derivatives were easily synthesized by the solid-phase method and conventional peptide modification techniques which includes, but is not limited to, N-acylation, C-amidation, cyclization, conservative substitution, or phosphorylation. The novel NAP derivatives of this invention are superior to NAP in stability, absorption, half-life, and drug exposure. Animal screening showed that these NAP derivatives have similar activities to NAP. The disclosed NAP derivatives have the potential to develop as medicaments for the treatment of Alzheimer's disease. Parkinson's disease, stroke, or cognitive impairment resulting from neural intoxication, neural injury, spinal injury, or coronary artery bypass surgery.

An embodiment of the invention provides an oligopeptide having the formula of:

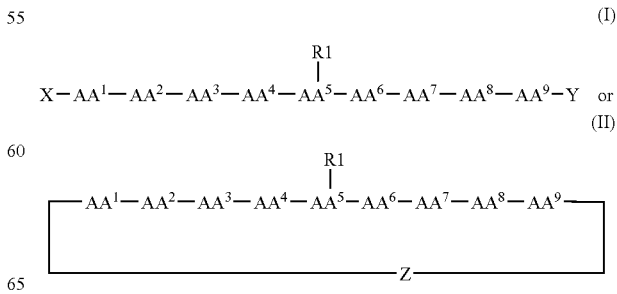

wherein each $AA^1$ and $AA^9$ is independently Asn or Gln;

each $AA^2$ and $AA^8$ is independently a bond, Ala, or Gly;

each $AA^3$ and $AA^7$ is independently Pro or homoproline (pipeconic acid);

each $AA^4$ and $AA^6$ is independently Val, Leu, or Ile;

$AA^5$ is Ser or Thr;

$R^1$ is hydrogen, phosphate, phosphate ester, sulfate, sulfate ester, or salt derivatives thereof;

X links to nitrogen of $AA^1$ and is hydrogen, $-COR^2$, $-COOR^3$, $-SO_2R^4$; wherein $R^2$, $R^3$, $R^4$ are each independently or together hydrogen, substituted or unsubstituted $C_{1-32}$ alkyl, substituted or unsubstituted $C_{2-32}$ alkenyl, substituted or unsubstituted $C_{2-32}$ alkynyl, substituted or unsubstituted $C_{6-18}$ aryl, or substituted or unsubstituted $C_{1-12}$ heteroaryl;

Y links to carbonyl group of $AA^9$ and is $-OR^5$, or $-NR^6R^7$; $R^5$, $R^6$, $R^7$ are each independently or together hydrogen, substituted or unsubstituted $C_{1-32}$ alkyl, substituted or unsubstituted $C_{2-32}$ alkenyl, substituted or unsubstituted $C_{2-32}$ alkynyl, substituted or unsubstituted $C_{6-18}$ aryl, or substituted or unsubstituted $C_{1-12}$ heteroaryl;

Z is a bond, or $AA^{10}$-D-$AA^{11}$, wherein $AA^{10}$ or $AA^{11}$ is Cys, Lys, or Asp, D is disulfide bond or amido group ($-CONH-$).

Also provided is an oligopeptide derivative for neural protection, regeneration, and repair. The oligopeptide derivative comprises the structure of the above described oligopeptides.

Further provided is a pharmaceutical composition for neural protection, regeneration, and repair. The pharmaceutical composition comprises an effective amount of the above described oligopeptide derivative and a pharmaceutically acceptable carrier.

In addition, use of the above described oligopeptide for the manufacture of a medicament for neural protection, regeneration, and repair in a subject is provided.

Moreover, a method for the treatment of Alzheimer's disease, Parkinson's disease, stroke, or cognitive impairment resulting from neural intoxication, neural injury, spinal injury, or coronary artery bypass surgery is provided. The method comprises administering a subject in need an effective amount of the above described pharmaceutical composition for neural protection, regeneration, and repair.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein:

FIG. 3A is BMEC-NAP0104; FIG. 3B is BMBC-NAP0105; FIG. 3C is BMEC-NAP0106; FIG. 3D is BMEC-NAP0107. The result of NAP is listed as reference.

FIG. 4A is BMEC-NAP0201; FIG. 4B is BMEC-NAP0401; FIG. 4C is BMEC-NAP0404; FIG. 4D is BMEC-NAP0407. The result of NAP is listed as reference.

FIG. 5A is BMEC-NAP0301; FIG. 5B is BMEC-NAP0303. The result of NAP is listed as reference.

FIG. 6A is BMEC-NAP0501; FIG. 6B is BMEC-NAP0502; FIG. 6C is BMEC-NAP0504; FIG. 6D is BMEC-NAP0507. The result of NAP is listed as reference.

FIG. 7A is BMEC-NAP0603; FIG. 7B is BMEC-NAP0604; FIG. 7C is BMEC-NAP0605; FIG. 7D is BMEC-NAP0606. The result of NAP is listed as reference.

FIG. 8A is BMEC-NAP0701; FIG. 8B is BMEC-NAP0706; FIG. 8C is BMEC-NAP0805; FIG. 8D is BMEC-NAP0806. The result of NAP is listed as reference.

FIG. 9A is NAP; FIG. 9B is BMEC-NAP0706.

DETAILED DESCRIPTION OF THE INVENTION

Figure 1:
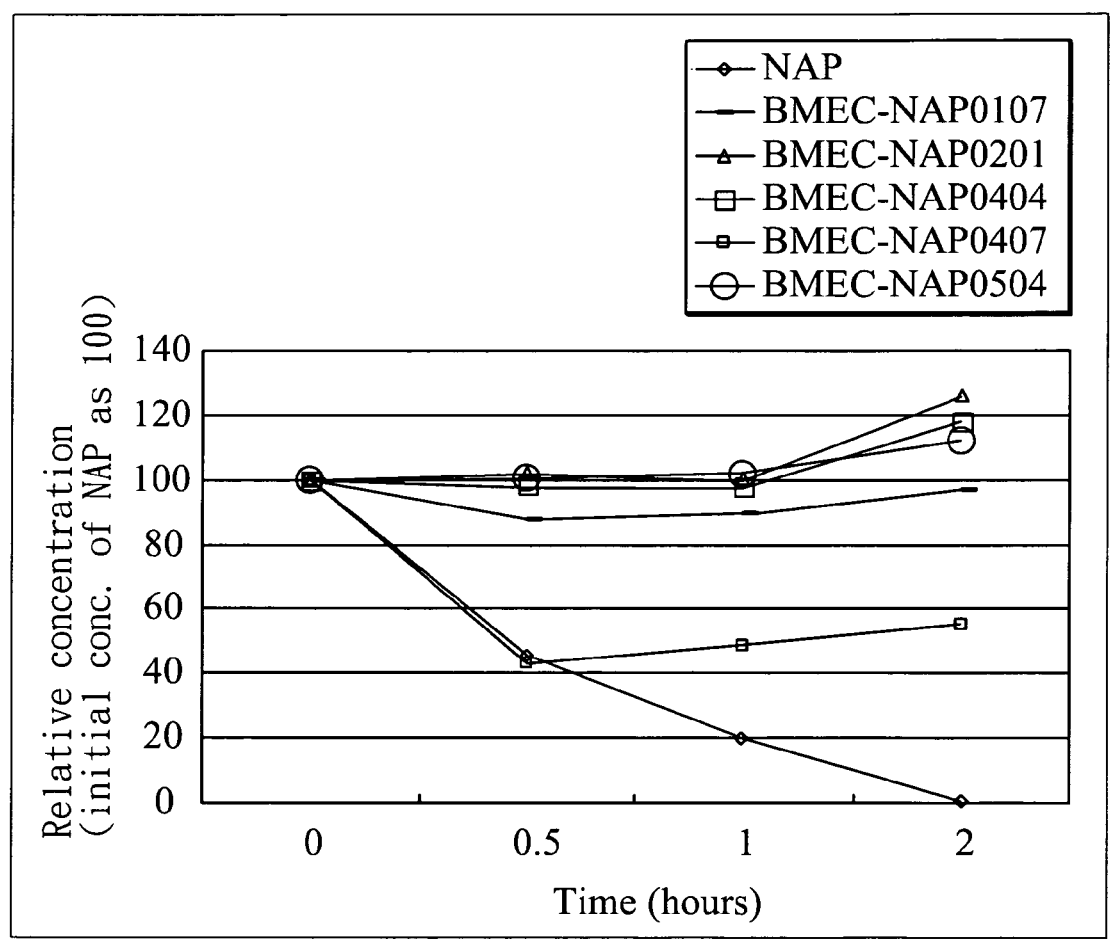
FIG. 1 is a diagram showing the ex vivo stability of the embodiments of the NAP derivatives (BMEC-NAP0107, BMEC-NAP0201, BMEC-NAP0404, BMEC-NAP0407, and BMEC-NAP0504), and NAP in rat sera.

The following description is of the best-contemplated mode of carrying out the invention. This description is made for the purpose of illustrating the general principles of the invention and should not be taken in a limiting sense. The scope of the invention is best determined by reference to the appended claims.

An oligopeptide, the oligopeptide derivative thereof, a pharmaceutical composition comprising the same, and a method using the same are provided.

A series of NAP derivatives were prepared by the conventional peptide modification techniques. The modification is as shown below. Peptide sequences shown are SEQ ID NOs: 4 and 5.

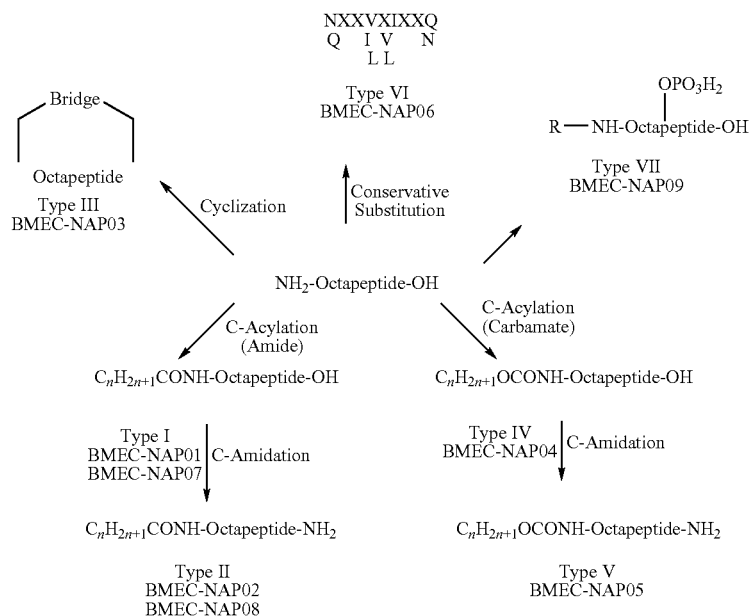

Specifically, the conventional modification includes, but is not limited to, N-acylation, C-amidation, cyclization, conservative substitution, or phosphorylation. The modified peptides are resistant to basic or acidic environments, enzyme degradation, and proteases. The prepared novel NAP derivatives have improved stability and prolonged half-life, enhancing the exposure of the drug to the living subject. N-acylation or C-amidation of NAP with lipophilic compounds may produce lipophilic NAP derivatives having increased absorbance, enhancing the exposure of the drug to the living subject. The NAP derivatives modified by N-acylation, C-amidation, cyclization, conservative substitution or phosphorylation may have simplified mechanisms of action by covering some pharmacophores possessing undesired effects, and a simple sigmoid curve of the concentration-activity relationship can be obtained.

Accordingly, an embodiment of the invention provides a oligopeptide having the formula of:

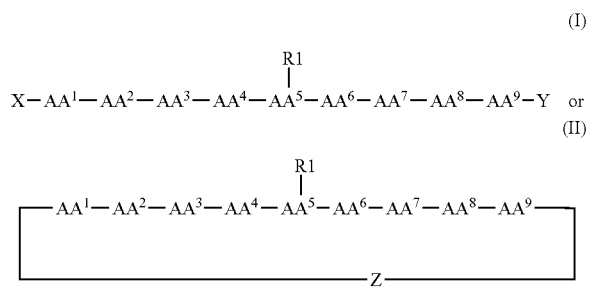

wherein
each $AA^1$ and $AA^9$ is independently Asn or Gln;
each $AA^2$ and $AA^8$ is independently a bond, Ala, or Gly;
each $AA^3$ and $AA^7$ is independently Pro or homoproline (pipeconic acid);
each $AA^4$ and $AA^6$ is independently Val, Leu, or Ile;
$AA^5$ is Ser or Thr;

$R^1$ is hydrogen, phosphate, phosphate ester, sulfate, sulfate ester, or salt derivatives thereof;

X links to nitrogen of $AA^1$ and is hydrogen, $-COR^2$, $-COOR^3$, $-SO_2R^4$; wherein $R^2$, $R^3$, $R^4$ are each independently or together hydrogen, substituted or unsubstituted $C_{1-32}$ alkyl, substituted or unsubstituted $C_{2-32}$ alkenyl, substituted or unsubstituted $C_{2-32}$ alkynyl, substituted or unsubstituted $C_{6-18}$ aryl, or substituted or unsubstituted $C_{1-12}$ heteroaryl;

Y links to carbonyl group of $AA^9$ and is $-OR^5$, or $-NR^6R^7$; $R^5$, $R^6$, $R^7$ are each independently or together hydrogen, substituted or unsubstituted $C_{1-32}$ alkyl, substituted or unsubstituted $C_{2-32}$ alkenyl, substituted or unsubstituted $C_{2-32}$ alkynyl, substituted or unsubstituted $C_{6-18}$ aryl, or substituted or unsubstituted $C_{1-12}$ heteroaryl;

Z is a bond, or $AA^{10}$-D-$AA^{11}$, wherein $AA^{10}$ or $AA^{11}$ is Cys, Lys, or Asp, D is disulfide bond or amido group (—CONH—).

Also provided is an oligopeptide derivative for neural protection, regeneration, and repair. The oligopeptide comprises the structure of the above described oligopeptide.

Further provided is a pharmaceutical composition for neural protection, regeneration, and repair. The pharmaceutical composition comprises an effective amount of the above described oligopeptide derivative and a pharmaceutically acceptable carrier.

In addition, use of the above described oligopeptide for the manufacture of a medicament for neural protection, regeneration, and repair in a subject is provided.

Moreover, a method for the treatmernt of Alzheimer's disease, Parkinson's disease, stroke, or cognitive impairment resulting from neural intoxication, neural injury, spinal injury, or coronary artery bypass surgery is provided. The method comprises administering a subject in need an effective amount of the above described pharmaceutical composition for neural protection, regeneration, and repair.

The terminology disclosed herein is illustrated below.

"$C_{1-32}$" indicates the carbon number of a substituent ranges from 1 to 32, and the other terms such as "$C_{2-32}$", "$C_{6-18}$", or "$C_{1-12}$" shall apply by analogy.

The "$C_{1-32}$ alkyl" used herein represents a linear or branched alkyl group with a carbon number of 1 to 30. Examples of the alkyl group include, but are not limited to, methyl, ethyl, propyl, isopropyl, n-butyl, isobutyl, tert-butyl, n-pentyl, 1-methylbutyl, 2-methylbutyl, 3-methylbutyl, 1-ethylpropyl, 1,1-dimethylpropyl, 1,2-dimethylpropyl, neopentyl, n-hexyl, 1-mehtylpentyl, 2-methylpentyl, 3-methylpentyl, 4-methylpentyl, 1-ethylbutyl, 2-ethylbutyl, 1,1-dimehtylbutyl, 1,2-dimethylbutyl, 1,3-dimehtylbutyl, 2,2-dimehtylbutyl, 2,3-dimethylbutyl, 3,3-dimehtylbutyl, 1,1,2-trimehtylpropyl, 1,2,2-trimehtylpropyl, 1-ehtyl-1-methylpropyl, 1-ethyl-2-methylpropyl, heptyl, 1-mehtylhexyl, 5-methylhexyl, 1,1-dimethylpentyl, 2,2-dimethylpentyl, 4,4-dimehtylpentyl, 1-ethylpentyl, 2-ethylpentyl, 1,1,3-timethylbutyl, 1,2,2-trimethylbutyl, 1,3,3-trimethylbutyl, 2,2,3-trimethylbutyl, 2,3,3-trimethylbutyl, 1-propylbutyl, 1,1,2,2-tetramethylpropyl, octyl, 1,methylheptyl, 3-methylheptyl, 6-methylheptyl, 2-ethylhexyl, 5,5-dimethylhexyl, 2,4,4-trimethylpentyl, 1-ethyl-1-methylpentyl, nonyl, 1-methyloctyl, 2-methyloctyl, 3-mehtyloctyl, 7-methyloctyl, 1-ethylheptyl, 1,1-methylheptyl, 6,6-dimethylheptyl, decyl, 1-methylnonyl, 2-methylnonyl, 6-methylnonyl, 1-ethyloctyl, 1-propylpentyl, n-nonyl, n-decyl, n-undecyl, n-dodecyl, n-tridecyl, n-tetradecyl, n-pentadecyl, or n-hexadecyl.

The "$C_{2-32}$ alkenyl" used herein represents a linear or branched alkenyl group with a carbon number of 2 to 32. Examples of the alkenyl group include, but are not limited to, vinyl, 1-allyl, isoallyl, 2-allyl, 1-butenyl, 1-methyl-1-allyl, 2-butenyl, 1-methyl-2-allyl, 3-butenyl, 2-methyl-1-allyl, 2-methyl-2-allyl, 1,3-butadienyl, 1-pentenyl, 1-et allyl, 2-pentenyl, 1-methyl-1-butenyl, 3-pentenyl, 1-methyl-2-butenyl, 4-pentenyl, 1-methyl-3-butenyl, 3-methyl-1-butenyl, 1,2-dimethyl-2-allyl, 1,1-dimethyl-2-allyl, 2-methyl-2-butenyl, 3-methyl-2-butenyl, 1,2-dimethyl-1-allyl, 2-methyl-3-butenyl, 3-methyl-3-butenyl, 1,3-pentadienyl, 1-vinyl-2-allyl, 1-hexenyl, 1-propyl-2-allyl, 2-hexenyl, 1-methyl-1-pentenyl, 1-ethyl-2-butenyl, 3-hexenyl, 4-hexenyl, 5-hexenyl, 1-methyl-4-pentenyl, 1-ethyl-3-butenyl, 1-isobutylvinyl, 1-ethyl-1-methyl-2-allyl, 1-ethyl-2-methyl-2-allyl, 1-isopropyl-2-allyl, 2-methyl-2-pentenyl, 3-methyl-3-pentenyl, 4-methyl-3-pentenyl, 1,3-dimethyl-2-butenyl, 1,1-dimethyl-3-butenyl, 3-methyl-4-pentenyl, 4-methyl-4-pentenyl, 1,2-dimethyl-3-butenyl, 1,3-dimethyl-3-butenyl, 1,1,2-trimethyl-2-allyl, 1,5-hexedinyl, 1-vinyl-3-butenyl, or 2,4-hexedienyl.

The "$C_{2-32}$ alkynyl" used herein represents a linear or branched alkynyl group with a carbon number of 2 to 32. Examples of the alkenyl group include, are not limited to, acetenyl, 1-propynyl, 2-propynyl, 1-butynyl, 1-methyl-2-propynyl, 2-butynyl, 3-butynyl, 1-pentynyl, 1-ethyl-2-propynyl, 2-pentynyl, 3-pentynyl, 1-methyl-2-butynyl, 4-peritynyl, 1-methyl-3-butynyl, 2-methyl-3-butenyl, 1-hexynyl, 1-n-propyl-2-propynyl, 2-hexynyl, 1-ethyl-2-butenyl, 3-hexenyl, 1-methyl-2-pentynyl, 1-methyl-3-pentynyl, 4-methyl-1-pentynyl, 3-methyl-1-pentynyl, 5-hexynyl, 1-ethyl-3-butynyl, 1-ethyl-1-methyl-2-propynyl, 1-isopropyl-2-propynyl, 1,1-dimehtyl-2-butynyl, or 2,2-dimethyl-3-butynyl.

The "$C_{6-18}$ aryl" used herein represents 6-C monocyclic, 10-C bicyclic, or 14-C tricyclic aryl ring systems, wherein each ring includes one to four substituents. Examples of the aryl group include, but are not limited to, phenyl, naphthyl, or anthracyl. The "$C_{1-12}$ heteroaryl" used herein represents aryl group of 5- to 8-membered monocyclic, 8- to 12-membered bicyclic, or 11- to 14-membered tricyclic ring systems including one or more heteroatoms such as O, N, or S. Examples of the heterocyclic group include, but are not limited to, pyridyl, fuiryl, imidazolyl, benzimidazolyl, pyrimidyl, thiaphenyl, quinolinyl, indolyl, or thiazolyl.

The alkyl, aryl, and heteroaryl groups used herein include saturated and unsaturated moieties. Examples of the substituents include, but are not limited to, halogen, hydroxyl, amido, cyano, nitro, mercapto, alkoxy carbonyl, amino, carboxyl, alkyl sulfonyl, alkyl carbonyl, carbamido, carbamino, thioureido, sulfmamido, alkyl, alkenyl, alkynyl, alkoxy, aryl, heteroaryl, cyclic, or heterocyclic; wherein alkyl, alkenyl, alkynyl, aryl, and heteroaryl group can be further substituted.

In one embodiment of the oligopeptide in the invention, $AA^2$ can be Ala, and $AA^8$ can be a bond or Ala. In addition, $R^1$ can be hydrogen or phosphate.

Specifically, in a first exemplary embodiment of the oligopeptide of the invention, the oligopeptide derivative is the BMEC-NAP01 series in Table 1. The BMEC-NAP01 series of the oligopeptide derivative represents a compound of formula (I) where X is —$COR^2$; Y is —OH; $R^1$ is hydrogen; $R^2$ is $C_3H_7$, $C_4H_9$, $C_5H^{11}$, $C_6H_{13}$, $C_8H_{17}$, $C_{10}H_{21}$, $C_{11}C_{23}$, $C_{16}H_{33}$, or $C_{19}H_{31}$. Preferably, in the BMEC-NAP01 series, $R^2$ is $C_4H_9$, $C_6H_{13}$, $C_8H_{17}$, or $C_{19}H_{31}$.

In a second exemplary embodiment of the oligopeptide of the invention, the oligopeptide derivative is the BMEC-NAP02 series in Table 1. The BMEC-NAP02 series of the oligopeptide derivative represents a compound of formula (I) where X is —$COR^2$; Y is —$NH_2$; $R^1$ is hydrogen; $R^2$ is $C_3H_7$, $C_5H_{11}$, $C_{11}C_{23}$, or $C_{19}H_{31}$. Preferably, in the BMEC-NAP02 series, $R^2$ is $C_3H_7$.

In a third exemplary embodiment of the oligopeptide of the invention, the oligopeptide derivative is the BMEC-NAP03 series in Table 1. The BMEC-NAP03 series of the oligopeptide derivative represents a compound of formula (II). In one embodiment of the BMEC-NAP03 series of the oligopeptide derivative, $R^1$ is hydrogen, Z is a bond; in another embodiment of the BMEC-NAP03 series of the oligopeptide derivative, $R^1$ is hydrogen; Z is $AA^{10}$-D-$AA^{11}$, wherein $AA^{10}$ and $AA^{11}$ are both Cys; and D is a disulfide bond. In yet another embodiment of the BMEC-NAP03 series of the oligopeptide derivative, $R^1$ is hydrogen; and Z is $AA^{10}$-D-$AA^{11}$, wherein one of $AA^{10}$ and $AA^{11}$ is Lys, the other is Asn, and D is amido group.

In a fourth exemplary embodiment of the oligopeptide of the invention, the oligopeptide derivative is the BMEC-NAP04 series shown in Table 1 is also provided. The BMEC-NAP04 series of the oligopeptide derivative represents a compound of formula (I) where X is —$COOR^3$; Y is —OH; $R^1$ is hydrogen; $R^3$ is $C_4H_9$, $C_6H_{13}$, $C_8H_{15}$, $C_{12}H_{25}$, or $C_{27}H_{46}$. Preferably, in the BMEC-NAP04 series, $R^3$ is $iC_4H_9$, $nC_6H_{13}$, or $C_{27}H_{46}$.

In a fifth exemplary embodiment of the oligopeptide of the invention, the oligopeptide is the BMEC-NAP05 series. The BMEC-NAP05 series of the oligopeptide derivative represents a compound of formula (I) where X is —$COOR^3$; Y is —$NH_2$; $R^1$ is hydrogen; $R^3$ is $C_4H_9$, $C_6H_{13}$, $C_8H_{15}$, $C_{12}H_{25}$, or $C_{27}H_{46}$. Preferably, in the BMEC-NAP05 series, $R^3$ is $iC_4H_9$, $nC_6H_{13}$, $iC_8H_{15}$, or $C_{27}H_{46}$.

In a sixth exemplary embodiment of the oligopeptide of the invention, the oligopeptide derivative is the BMEC-NAP06 series. The BMEC-NAP06 series of the oligopeptide derivative represents a compound of formula (I) where X is hydrogen; Y is —OH; $R^1$ is hydrogen; the sequence of $AA^1$-$AA^2$-$AA^3$-$AA^4$-$AA^5$-$AA^6$-$AA^7$-$AA^8$-$AA^9$ include, but is not limited to NAPVSIPAQ (SEQ ID NO: 6), QAPVSIPQ (SEQ ID NO: 7), NAPVSIPN (SEQ ID NO: 8), NAPVSLPQ (SEQ ID NO: 9), NAPVSVPQ (SEQ ID NO: 10), NAPVSLPQ (SEQ ID NO: 11), QAPVSVPAQ (SEQ ID NO: 12), or NAPISIPAN (SEQ ID NO: 13). Preferably, in the BMEC-NAP06 series, the sequence of $AA^1$-$AA^2$-$AA^3$-$AA^4$-$AA^5$-$AA^6$-$AA^7$-$AA^8$-$AA^9$ is NAPVSIPN (SEQ ID NO: 14), NAPISIPQ (SEQ ID NO: 15), NAPVSVPQ (SEQ ID NO: 16), or NAPVSLPQ (SEQ ID NO: 11).

In a seventh exemplary embodiment of the oligopeptide of the invention, the oligopeptide derivative is the BMEC-NAP07 series. The BMEC-NAP07 series of the oligopeptide derivative represents a compound of formula (I) where X is benzoyl, α-naphthoyl, 4-phenylbenzoyl, 2-thiophenecarbonyl, bezyloxycarbonyl (Cbz), or fluorenylmethyloxycarbonyl (Fmoc); Y is —OH; $R^1$ is hydrogen. Preferably, in the BMEC-NAP07 series, X is benzoyl, or fluorenylmethyloxycarbonyl (Fmoc).

In an eighth exemplary embodiment of the oligopeptide of the invention, the oligopeptide derivative is the BMEC-NAP08 series. The BMEC-NAP08 series of the oligopeptide derivative represents a compound of formula (I) where X is benzoyl, α-naphthoyl, 4-phenylbenzoyl, 2-thiophenecarbonyl, bezyloxycarbonyl (Cbz), or fluorenylmethyloxycarbonyl (Fmoc); Y is —NH$_2$; $R^1$ is hydrogen. Preferably, in the BMEC-NAP08 series; X is bezyloxycarbonyl (Cbz) or fluorenylmethyloxycarbonyl (Fmoc).

In a ninth exemplary embodiment of the oligopeptide of the invention, the oligopeptide derivative is the BMEC-NAP09 series. The BMEC-NAP09 series of the oligopeptide derivative represents a compound of formula (I). In one embodiment of the BMEC-NAP09 series of the oligopeptide derivative, X is fluorescein-5(6)-carbonyl (5(6)-FAM); Y is —OH; $R^1$ is hydrogen. In another embodiment of the BMEC-NAP09 series of the oligopeptide derivative, X is hydrogen; Y is —OH; and $R^1$ is phosphate.

In an exemplary embodiment of the pharmaceutical composition, "an effective amount" means that the amount is sufficient to achieve a beneficial result while being administered to a subject in need, or the amount of the compound provides a desired activity in vitro or in vivo. The specific effective amount of the compound administered to the subject depends on the particular condition and severity of the disease or symptoms, and the physical condition of the subject, such as the general health status, age, gender, body weight, and the tolerance to the compound. A skilled physician may determine the appropriate dosage based on these and other factors. The composition may, for example, be in a form suitable for oral administration as a tablet, capsule, pill, powder, sustained release formulations, solution, or suspension; for parenteral injection as a sterile solution, suspension or emulsion. Parenteral administration includes, for example, systemic administration, such as intramuscular, intravenous, subcutaneous, or intraperitoneal injection. According to the form of the disease, the compound can be orally administered; externally applied; intrathecally, intranasally, or orally inhaled; or intrarectally administered. Oral administration or injection is preferred.

The oligopeptide of the invention can be formulated with pharmaceutically acceptable carriers, adjuvants, diluents, excipients, or solvents. For convenience, the "carrier" includes all carriers, adjuvants, diluents, excipients, solvents, or other inert additives. The formulations of the compound vary with the administration routs and the diseases, symptoms, or disorders to be treated. Suitable pharmaceutically acceptable carriers include components inert to the compound. Standard pharmaceutical formulations can be applied as described in, for example, Remington's Pharmaceutical Sciences, Mack Publishing Company, Easton, Pa. Suitable pharmaceutically acceptable carriers for injection include, for example, sterile water, normal saline, saline containing about 0.9% mg/ml of benzyl alcohol, phosphate buffered saline, Hank's solution, or Ringer's lactated solution. Methods for capsulation such as covering in hard gelatin or cyclodextran are well-known in the art (Baker, et al., "Controlled Release of Biological active Agents", John Wiley and Sons, 1986).

In the following tables of this disclosure, for example, N is Asparagine (Asn), A is Alanine (Ala), P is Proline (Pro), V is Valine (Val), S is Serine (Ser), I is Isoleucine (Ile), Q is Glutamine (Gln), L is Leucine (Leu), iBu is isobutyl group, iOct is isooctyl group (2-ethylhexyl), nBu is norbutyl group, nHex is norhexyl group, nOct is noroctyl group, nDod is nordedocyl group, Cbz represents

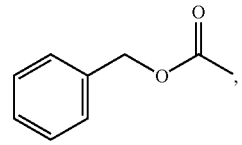

Fmoc represents

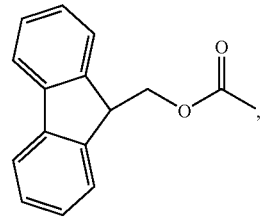

fluorescein-5(6)-carbonyl (5(6)-FAM) represents

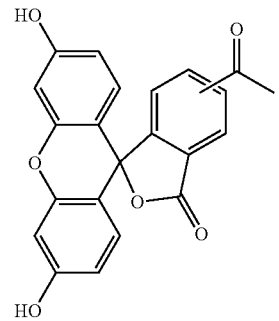

Practical examples are described herein.

EXAMPLES

Example 1

Synthesis of NAP Derivatives

The NAP derivatives were prepared by conventional solid phase synthesis and peptide modification techniques. Specifically, the NAP derivatives were prepared with standard Merrifield solid phase synthesis by DigitalGene Biosciences Co., Ltd.; Taipei, ROC; http://www.digitalgene.com.tw), AC Scientific Inc. (Duluth, Ga., USA; http://www.acscientific.com), and C S Bio Co. (Menlo Park, Calif., USA; http://www.csbio.com). Raw NAP derivatives were isolated from the resin of the solid phase synthesis and purified by preparative reverse phase HPLC to achieve a purity of over 95%. The molecular weight thereof was determined by LC-Mass spectrometry. The sequences, theoretical and practical molecular weight of the prepared NAP derivatives were listed in Table 1.

TABLE 1

Sequences and theoretical and practical molecular weight of NAP derivatives

| No. | Sequence | Theoretical M.W. | Practical M.W. |
|---|---|---|---|
| BMEC-NAP | H-NAPVSIPQ-OH (NAPVSIPQ is SEQ ID NO: 3) | 824.9 | 824.0 |
| BMEC-NAP0101 | Butyryl-NAPVSIPQ-OH (NAPVSIPQ is SEQ ID NO: 3) | 894.0 | 894.0 |
| BMEC-NAP0102 | Adipyl-NAPVSIPQ-OH (NAPVSIPQ is SEQ ID NO: 3) | 922.0 | 922.0 |
| BMEC-NAP0103 | Lauryl-NAPVSIPQ-OH (NAPVSIPQ is SEQ ID NO: 3) | 1006.3 | 1006.0 |
| BMEC-NAP0104 | Arachidyl-NAPVSIPQ-OH (NAPVSIPQ is SEQ ID NO: 3) | 1110.5 | 1110.0 |
| BMEC-NAP0105 | $C_4H_9$CO-NAPVSIPQ-OH (NAPVSIPQ is SEQ ID NO: 3) | 908.1 | 909.0 |
| BMEC-NAP0106 | $C_6H_{13}$CO-NAPVSIPQ-OH (NAPVSIPQ is SEQ ID NO: 3) | 936.0 | 936.0 |
| BMEC-NAP0107 | $C_8H_{17}$CO-NAPVSIPQ-OH (NAPVSIPQ is SEQ ID NO: 3) | 964.0 | 964.0 |
| BMEC-NAP0108 | $C_{10}H_{21}$CO-NAPVSIPQ-OH (NAPVSIPQ is SEQ ID NO: 3) | 992.0 | 992.0 |
| BMEC-NAP0109 | $C_{16}H_{33}$CO-NAPVSIPQ-OH (NAPVSIPQ is SEQ ID NO: 3) | 1076.5 | 1077.0 |
| BMEC-NAP0201 | Butyryl-NAPVSIPQ-$NH_2$ (NAPVSIPQ is SEQ ID NO: 3) | 893.0 | 893.0 |
| BMEC-NAP020 | Adipyl-NAPVSIPQ-$NH_2$ (NAPVSIPQ is SEQ ID NO: 3) | 921.0 | 921.0 |
| BMEC-NAP0203 | Lauryl-NAPVSIPQ-$NH_2$ (NAPVSIPQ is SEQ ID NO: 3) | 1005.3 | 1006.0 |
| BMEC-NAP0204 | Arachidyl-NAPVSIPQ-$NH_2$ (NAPVSIPQ is SEQ ID NO: 3) | 1109.5 | 1110.0 |
| BMEC-NAP0301 | Cyclo-(NAPVSIPQ) (NAPVSIPQ is SEQ ID NO: 3) | 806.4 | 806.0 |
| BMEC-NAP0302 | C—NAPVSIPQ—C<br>\|                  \|<br>S————————S<br>(NAPVSIPQ is SEQ ID NO: 3) | 1029.4 | 1029.0 |
| BMEC-NAP0303 | K—NAPVSIPQ—D<br>\|                  \|<br>HN————————CO<br>(NAPVSIPQ is SEQ ID NO: 3) | 1050.5 | 1050.3 |
| BMEC-NAP0401 | iBu-OCO-NAPVSIPQ-OH (NAPVSIPQ is SEQ ID NO: 3) | 924.0 | 924.0 |
| BMEC-NAP0402 | iOct-OCO-NAPVSIPQ-OH (NAPVSIPQ is SEQ ID NO: 3) | 981.0 | 981.0 |
| BMEC-NAP0403 | nBu-OCO-NAPVSIPQ-OH (NAPVSIPQ is SEQ ID NO: 3) | 924.0 | 924.0 |
| BMEC-NAP0404 | nHex-OCO-NAPVSIPQ-OH (NAPVSIPQ is SEQ ID NO: 3) | 952.0 | 952.0 |
| BMEC-NAP0405 | nOct-OCO-NAPVSIPQ-OH (NAPVSIPQ is SEQ ID NO: 3) | 981.0 | 980.0 |
| BMEC-NAP0406 | nDod-OCO-NAPVSIPQ-OH (NAPVSIPQ is SEQ ID NO: 3) | 1037.0 | 1037.0 |
| BMEC-NAP0407 | Cholesteryl-OCO-NAPVSIPQ-OH (NAPVSIPQ is SEQ ID NO: 3) | 1237.0 | 1237.0 |
| BMEC-NAP0501 | iBu-OCO-NAPVSIPQ-$NH_2$ (NAPVSIPQ is SEQ ID NO: 3) | 923.0 | 923.0 |
| BMEC-NAP0502 | iOct-OCO-NAPVSIPQ-$NH_2$ (NAPVSIPQ is SEQ ID NO: 3) | 980.0 | 980.0 |
| BMEC-NAP0503 | nBu-OCO-NAPVSIPQ-$NH_2$ (NAPVSIPQ is SEQ ID NO: 3) | 923.0 | 923.0 |
| BMEC-NAP0504 | nHex-OCO-NAPVSIPQ-$NH_2$ (NAPVSIPQ is SEQ ID NO: 3) | 951.0 | 951.0 |
| BMEC-NAP0505 | nOct-OCO-NAPVSIPQ-$NH_2$ (NAPVSIPQ is SEQ ID NO: 3) | 980.0 | 980.0 |

TABLE 1-continued

Sequences and theoretical and practical molecular weight of NAP derivatives

| No. | Sequence | Theoretical M.W. | Practical M.W. |
|---|---|---|---|
| BMEC-NAP0506 | nDod-OCO-NAPVSIPQ-NH$_2$ (NAPVSIPQ is SEQ ID NO: 3) | 1036.0 | 1036.0 |
| BMEC-NAP0507 | Cholesteryl-OCO-NAPVSIPQ-NH$_2$ (NAPVSIPQ is SEQ ID NO: 3) | 1236.0 | 1236.0 |
| BMEC-NAP0601 | H-NAPVSIPAQ-OH (NAPVSIPAQ is SEQ ID NO: 6) | 895.5 | 895.3 |
| BMEC-NAP0602 | H-QAPVSIPQ-OH (QAPVSIPQ is SEQ ID NO: 7) | 839.1 | 838.1 |
| BMEC-NAP0603 | H-NAPVSIPN-OH (NAPVSIPN is SEQ ID NO: 8) | 811.0 | 810.1 |
| BMEC-NAP0604 | H-NAPISIPQ-OH (NAPISIPQ is SEQ ID NO: 9) | 839.1 | 838.6 |
| BMEC-NAP0605 | H-NAPVSVPQ-OH (NAPVSVPQ is SEQ ID NO: 10) | 811.0 | 810.1 |
| BMEC-NAP0606 | H-NAPVSLPQ-OH (NAPVSLPQ is SEQ ID NO: 11) | 825.1 | 824.9 |
| BMEC-NAP0607 | H-QAPVSVPAQ-OH (QAPVSVPAQ is SEQ ID NO: 12) | 896.1 | 897.2 |
| BMEC-NAP0608 | H-NAPISIPAN-OH (NAPISIPAN is SEQ ID NO: 13) | 896.1 | 896.3 |
| BMEC-NAP0701 | Benzoyl-NAPVSIPQ-OH (NAPVSIPQ is SEQ ID NO: 3) | 929.1 | 928.8 |
| BMEC-NAP0702 | α-Naphthoyl-NAPVSIPQ-OH (NAPVSIPQ is SEQ ID NO: 3) | 979.1 | 978.9 |
| BMEC-NAP0703 | 4-Phenylbenzoyl-NAPVSIPQ-OH (NAPVSIPQ is SEQ ID NO: 3) | 1005.2 | 1004.7 |
| BMEC-NAP0704 | 2-Thiophenecarbonyl-NAPVSIPQ-OH (NAPVSIPQ is SEQ ID NO: 3) | 935.1 | 934.5 |
| BMEC-NAP0705 | Cbz-NAPVSIPQ-OH (NAPVSIPQ is SEQ ID NO: 3) | 959.2 | 958.5 |
| BMEC-NAP0706 | Fmoc-NAPVSIPQ-OH (NAPVSIPQ is SEQ ID NO: 3) | 1047.2 | 1046.7 |
| BMEC-NAP0801 | Benzoyl-NAPVSIPQ-NH$_2$ (NAPVSIPQ is SEQ ID NO: 3) | 928.1 | 927.6 |
| BMEC-NAP0802 | α-Naphthoyl-NAPVSIPQ-NH$_2$ (NAPVSIPQ is SEQ ID NO: 3) | 978.0 | 977.6 |
| BMEC-NAP0803 | 4-Phenylbenzoyl-NAPVSIPQ-NH$_2$ (NAPVSIPQ is SEQ ID NO: 3) | 1004.2 | 1003.7 |
| BMEC-NAP0804 | 2-Thiophenecarbonyl-NAPVSIPQ-NH$_2$ (NAPVSIPQ is SEQ ID NO: 3) | 934.1 | 933.7 |
| BMEC-NAP0805 | Cbz-NAPVSIPQ-NH$_2$ (NAPVSIPQ is SEQ ID NO: 3) | 958.1 | 957.6 |
| BMEC-NAP0806 | Fmoc-NAPVSIPQ-NH$_2$ (NAPVSIPQ is SEQ ID NO: 3) | 1046.2 | 1045.7 |
| BMEC-NAP9901 | 5(6)FAM-NAPVSIPQ-OH (NAPVSIPQ is SEQ ID NO: 3) | 1182.9 | 1183.0 |
| BMEC-NAP9902 | NH$_2$-NAPVS(OPO$_3$H$_2$)IPQ-OH | 904.0 | 904.0 |

Example 2

Stability of NAP Derivatives

The stability of the NAP derivatives prepared by EXAMPLE 1 was measured with the system of human colon cancer cell, Caco-2 cell. Caco-2 cells (1×10$^5$ cells) were first seeded into a polycarbonate film on the upper layer of a 12-well Transwell and incubated for 18 to 26 days at 37° C. The TEER of the Caco-2 cell monolayer was measured over 350 Ω×cm$^2$. The stability of the NAP derivatives in the Hanks' balanced salt solutions (HBSS) was measured by the concentration changes of NAP and the NAP derivatives incubated in the HBSS at 37° C. for 4 hours. The stability of the NAP derivatives in the Caco-2 cell system was measured by the procedure described below. NAP and the NAP derivatives in the HBSS were added into the upper layer of the Caco-2 cell-seeded Transwell. After 4-hour incubation, the concentration of NAP and the NAP derivatives in the upper and lower layers was measured and analyzed in comparison with the initial concentration (500 μM) by reverse HPLC at 210 nm. The results of NAP and the NAP derivatives were listed in Table 2.

TABLE 2

Stability of NAP derivatives in the HBSS and the Caco-2 cell system.

| No. | Initial conc. in HBSS | Conc. after 4-hour in HBSS | Conc. after 4-hour in Caco-2 cells |
|---|---|---|---|
| BMEC-NAP | 100.00 | 99.21 | 42.49 |
| BMEC-NAP0101 | 100.00 | 97.76 | 56.02 |
| BMEC-NAP0102 | 100.00 | 99.95 | 60.72 |
| BMEC-NAP0105 | 100.00 | 98.36 | 49.86 |
| BMEC-NAP0106 | 100.00 | 102.05 | 26.74 |
| BMEC-NAP0107 | 100.00 | 98.74 | 24.21 |
| BMEC-NAP0201 | 100.00 | 100.39 | 94.18 |
| BMEC-NAP0202 | 100.00 | 98.38 | 95.59 |

TABLE 2-continued

Stability of NAP derivatives in the HBSS and the Caco-2 cell system.

| No. | Initial conc. in HBSS | Conc. after 4-hour in HBSS | Conc. after 4-hour in Caco-2 cells |
|---|---|---|---|
| BMEC-NAP0301 | 100.00 | 100.72 | 94.72 |
| BMEC-NAP0302 | 100.00 | 106.35 | 81.33 |
| BMEC-NAP0303 | 100.00 | 98.49 | 57.19 |
| BMEC-NAP0401 | 100.00 | 100.02 | 52.63 |
| BMEC-NAP0402 | 100.00 | 98.91 | 18.92 |
| BMEC-NAP0403 | 100.00 | 98.49 | 29.05 |
| BMEC-NAP0404 | 100.00 | 99.16 | 29.87 |
| BMEC-NAP0405 | 100.00 | 99.66 | 17.11 |
| BMEC-NAP0406 | 100.00 | 130.04 | 97.75 |
| BMEC-NAP0501 | 100.00 | 100.17 | 87.00 |
| BMEC-NAP0502 | 100.00 | 99.25 | 82.37 |
| BMEC-NAP0503 | 100.00 | 99.77 | 85.89 |
| BMEC-NAP0504 | 100.00 | 100.22 | 82.71 |
| BMEC-NAP0505 | 100.00 | 93.41 | 76.83 |
| BMEC-NAP0602 | 100.00 | 104.94 | 21.81 |
| BMEC-NAP0603 | 100.00 | 101.90 | 29.17 |
| BMEC-NAP0604 | 100.00 | 103.83 | 23.89 |
| BMEC-NAP0605 | 100.00 | 104.25 | 27.76 |
| BMEC-NAP0606 | 100.00 | 99.42 | 11.54 |
| BMEC-NAP0607 | 100.00 | 97.33 | 16.54 |
| BMEC-NAP0608 | 100.00 | 110.89 | 30.58 |
| BMEC-NAP0701 | 100.00 | 98.62 | 78.97 |
| BMEC-NAP0702 | 100.00 | 96.55 | 61.61 |
| BMEC-NAP0703 | 100.00 | 95.73 | 88.79 |
| BMEC-NAP0704 | 100.00 | 99.88 | 73.69 |
| BMEC-NAP0705 | 100.00 | 100.00 | 72.93 |
| BMEC-NAP0706 | 100.00 | 99.78 | 67.14 |
| BMEC-NAP0801 | 100.00 | 99.88 | 92.58 |
| BMEC-NAP0802 | 100.00 | 100.00 | 88.68 |
| BMEC-NAP0804 | 100.00 | 98.62 | 92.09 |
| BMEC-NAP0805 | 100.00 | 98.58 | 89.54 |
| BMEC-NAP0806 | 100.00 | 100.00 | 76.24 |
| BMEC-NAP9901 | 100.00 | 99.86 | 81.63 |
| BMEC-NAP9902 | 100.00 | 98.80 | 94.19 |

As shown in Table 2, the NAP derivatives prepared by EXAMPLE 1 were very stable in the HBSS and the Caco-2 cell system, indicating these peptides can be stored under general conditions. It was found that NAP and the NAP derivatives having OH group at the C-terminus, such as BMEC-NAP01, BMEC-NAP04, and BMEC-NAP06, could be degraded in the Caco-2 cell system after 4-hour incubation. The residual concentration of these peptides was 20 to 60% of the initial concentration thereof. However, the NAP derivatives having amidation at C-terminus such as BMEC-NAP02 and BMEC-NAP05, cyclization such as BMEC-NAP03, or modification using lipophilic aryl group such as BMEC-NAP07 and MEC-NAP08 may have increased stability in the presence of the cells.

The stability of NAP and the NAP derivative such as BMEC-NAP0107, BMEC-NAP0201, BMEC-NAP0404, BMEC-NAP0407, and BMEC-NAP0504 were further analyzed in rat sera ex vivo. Thirty μl of NAP and the NAP derivatives in 5 mM buffer was added to 0.8 ml of rat serum and incubated in water bath at 37° C. One hundred μl of the mixture was sampled at 0-, 0.5-, 1-, and 2-hr incubation and diluted with 100 μl of ACN-MeOH solution. The mixture was frozen to −20° C. and centrifuged with 10000 rpm at 4° C. for 5 minutes. The relative concentration was measured by LC-Mass spectrometry (Waters 2795 HT Separations Module/Waters Quattro Ultima/MassLynx3.5). The stability results of BMEC-NAP0107, BMEC-NAP0201, BMEC-NAP0404, BMEC-NAP0407, BMEC-NAP0504, and NAP were shown in FIG. 1. The initial concentration was defined as 100. The results show that the embodiments of the NAP derivatives in the invention have excellent stability in comparison with NAP, indicating these peptides have a prolonged retention rate in the living organism and may prolong the effect and reduce the interval of administration.

Example 3

Permeation of the NAP Perivatives

The permeation of NAP and the NAP derivatives was examined using the Caco-2 cell system. Caco-2 cells ($1 \times 10^5$ cells) were seeded into the polycarbonate film on the upper layer of a 12-well Transwell and incubated at 37° C. for 18 to 26 days. The TEER of the Caco cell monolayer was measured over 350 $\Omega \times cm^2$. NAP and the NAP derivatives in the HBSS were added into the upper layer of the Caco-2 cell-seeded Transwell. After 4-hour incubation, the concentration of NAP and the NAP derivatives in the upper and lower layers was measured and analyzed in comparison with the initial concentration (500 μM) by reverse phase HPLC at 210 nm.

The permeation results of NAP and the NAP derivatives to the Caco-2 cell monolayer were listed in Table 3.

TABLE 3

Permeation of the NAP derivatives to Caco-2 cell monolayer

| No. | Conc. at the lover layer | NAP results of the same batch of cells |
|---|---|---|
| BMEC-NAP0201 | 0.12 | 0.00 |
| BMEC-NAP0202 | 0.82 | 0.00 |
| BMEC-NAP0301 | 0.35 | 0.26 |
| BMEC-NAP0302 | 1.28 | 0.26 |
| BMEC-NAP0401 | 0.24 | 0.1 |
| BMEC-NAP0402 | 2.02 | 0.1 |
| BMEC-NAP0404 | 2.00 | 0.1 |
| BMEC-NAP0501 | 0.76 | 0.06 |
| BMEC-NAP0502 | 1.39 | 0.1 |
| BMEC-NAP0503 | 0.60 | 0.06 |
| BMEC-NAP0504 | 0.49 | 0.06 |
| BMEC-NAP0505 | 0.65 | 0.06 |
| BMEC-NAP0601 | 0.07 | 0.26 |
| BMEC-NAP0603 | 0.04 | 0.03 |
| BMEC-NAP0701 | 0.28 | 0.00 |
| BMEC-NAP0702 | 0.27 | 0.00 |
| BMEC-NAP0704 | 0.24 | 0.00 |
| BMEC-NAP0705 | 0.21 | 0.00 |
| BMEC-NAP0706 | 0.57 | 0.00 |
| BMEC-NAP0801 | 0.33 | 0.00 |
| BMEC-NAP0802 | 0.34 | 0.00 |
| BMEC-NAP0804 | 0.31 | 0.00 |
| BMEC-NAP0805 | 0.27 | 0.00 |
| BMEC-NAP9901 | 0.77 | 0.00 |

The results show that the NAP derivatives such as BMEC-NAP02, BMEC-NAP03, BMEC-NAP04, BMEC-NAP05, BMEC-NAP06, BMEC-NAP07, BMEC-NAP08, and BMEC-NAP99 have better permeation than NAP.

Example 4

Neural Protection of the NAP Derivatives

Figure 2:
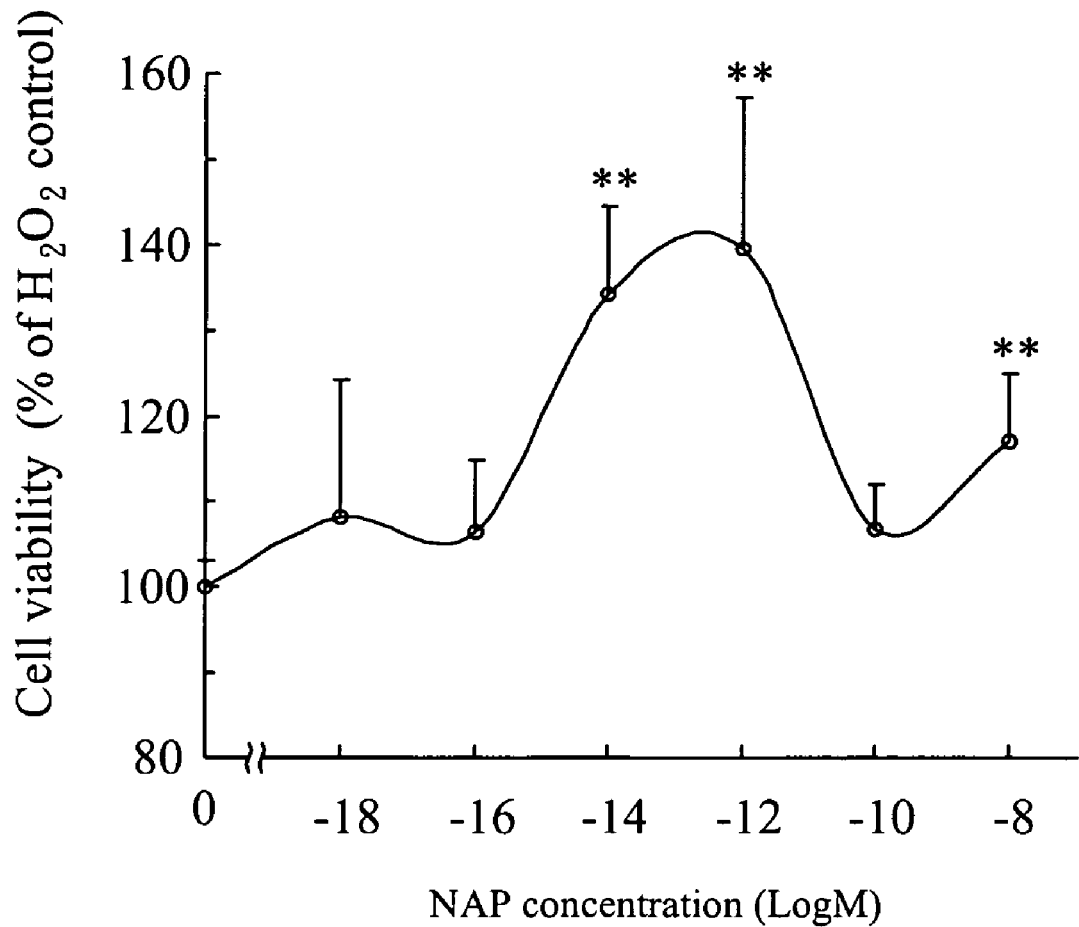
FIG. 2 is a diagram showing the neural protection of NAP in an $H_2O_2$/PC12 screening system.
Figure 3A:
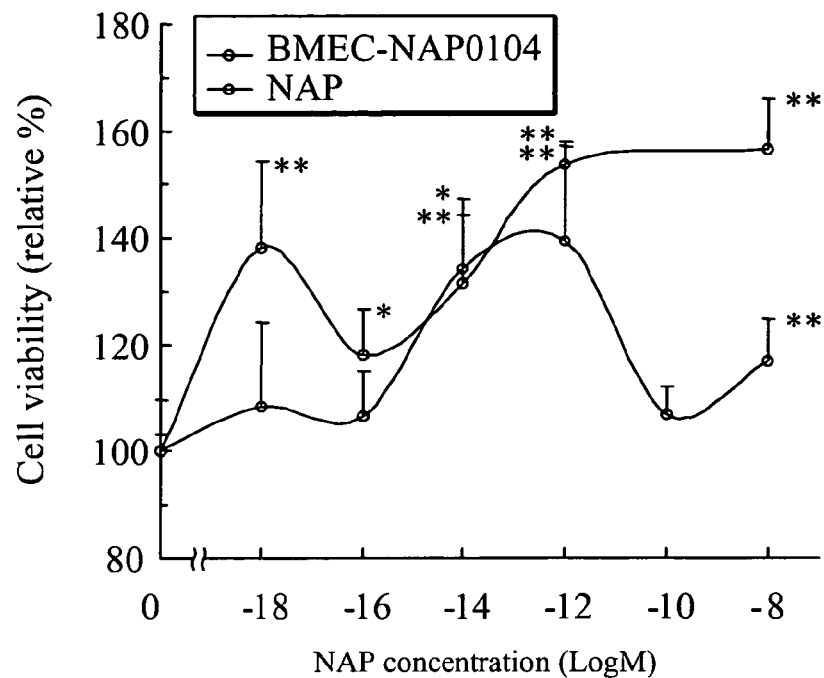
FIGS. 3A to 3D are diagrams showing neural protection of BMEC-NAP01 series of the embodiments of the NAP derivatives.
Figure 3B:
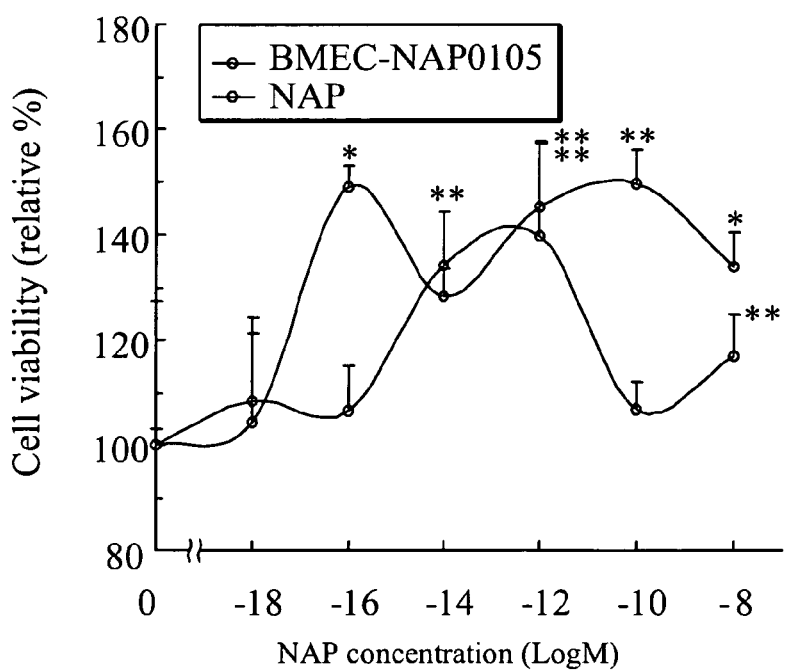
Figure 3C:
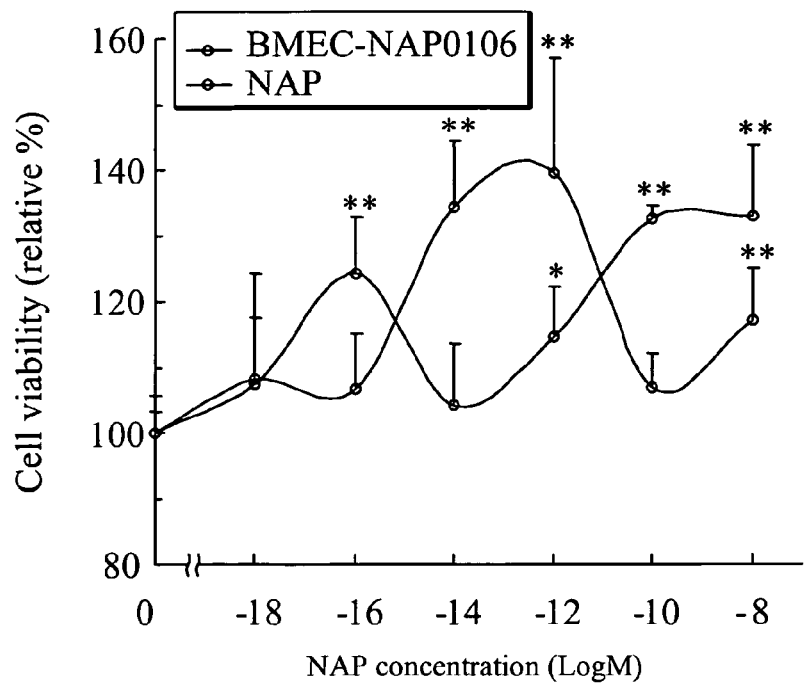
Figure 3D:
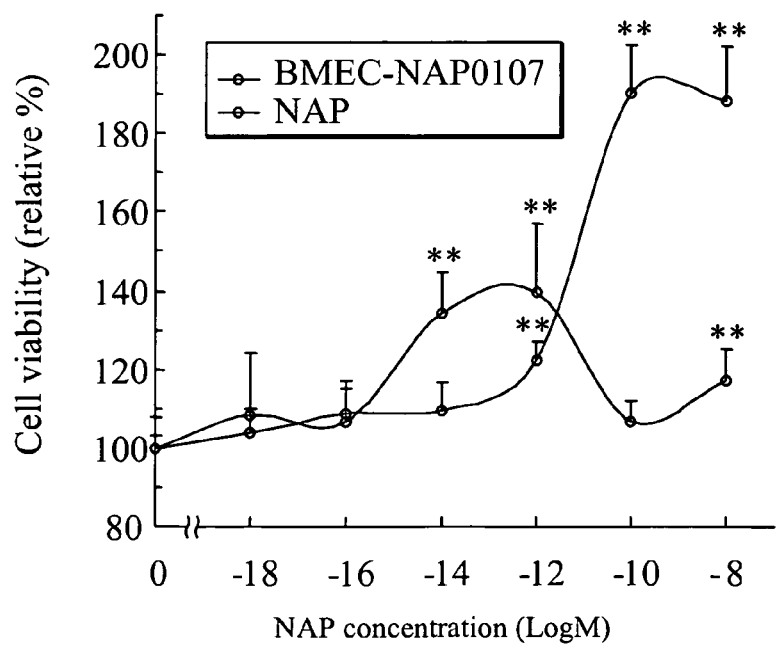
Figure 4A:
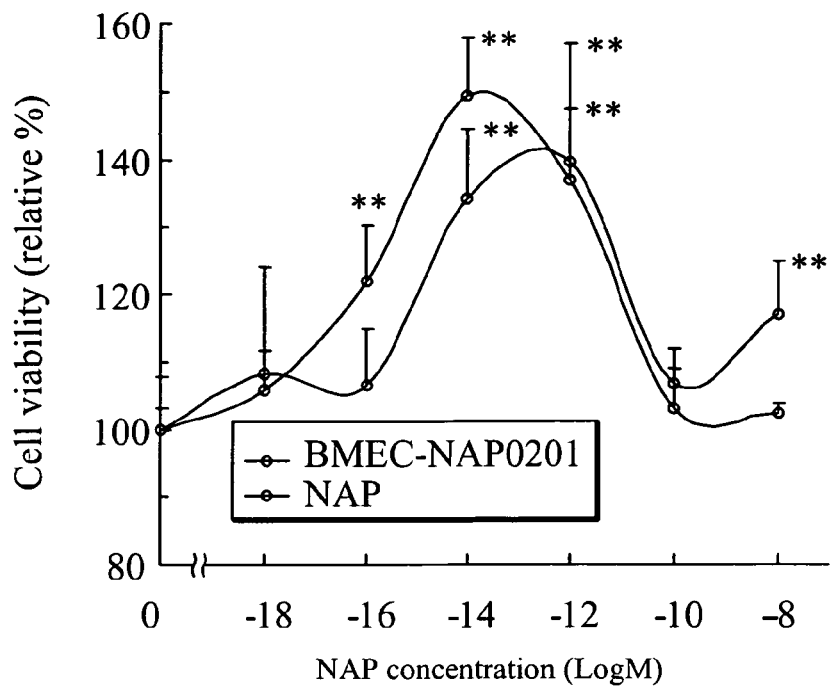
FIGS. 4A to 4D are diagrams showing the neural protection of BMEC-NAP02 series and BMEC-NAP04 series of the embodiments of the NAP derivatives.
Figure 4B:
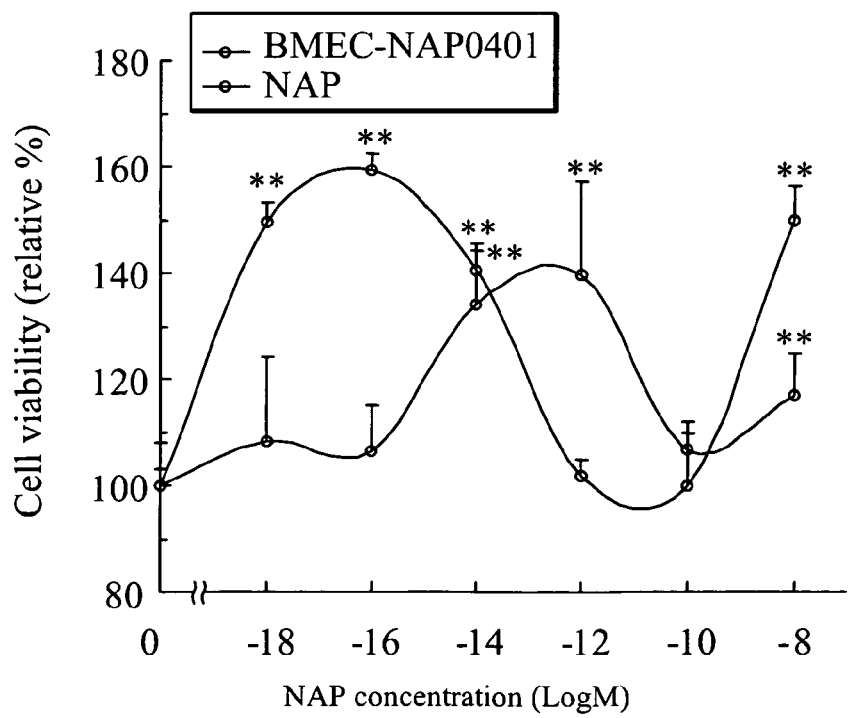
Figure 4C:
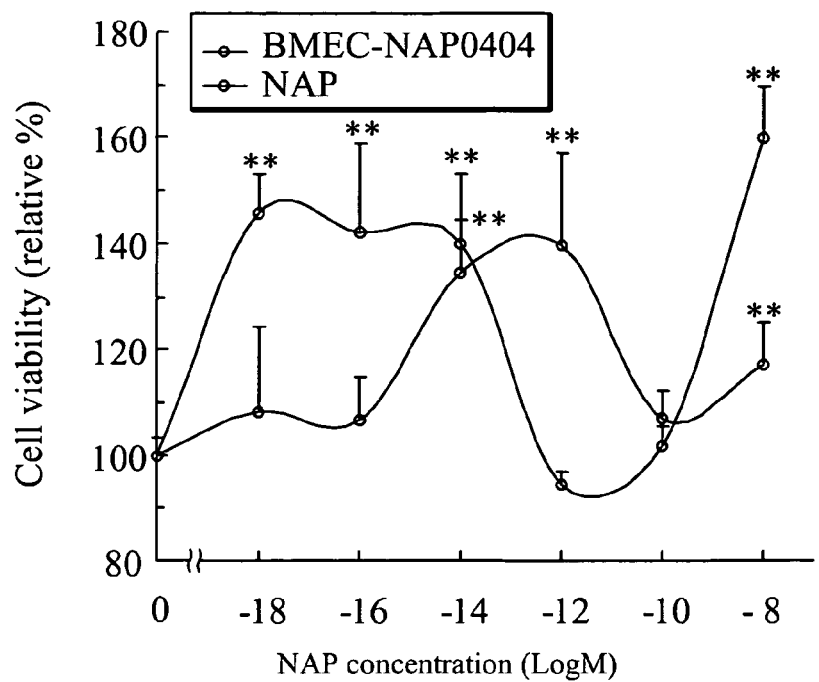
Figure 4D:
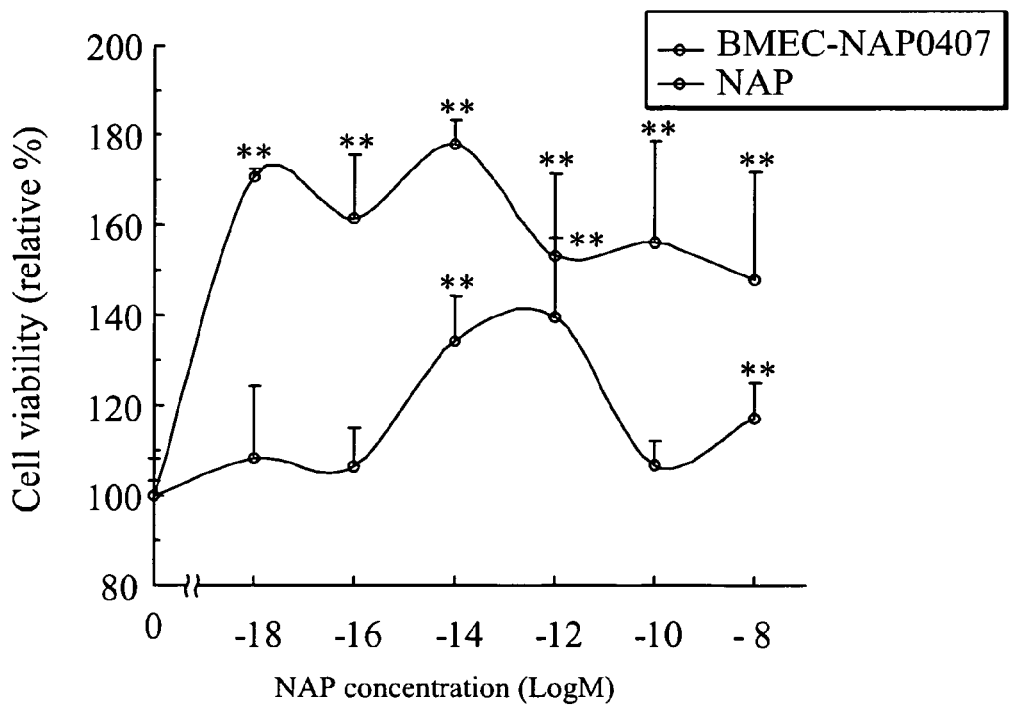
Figure 5A:
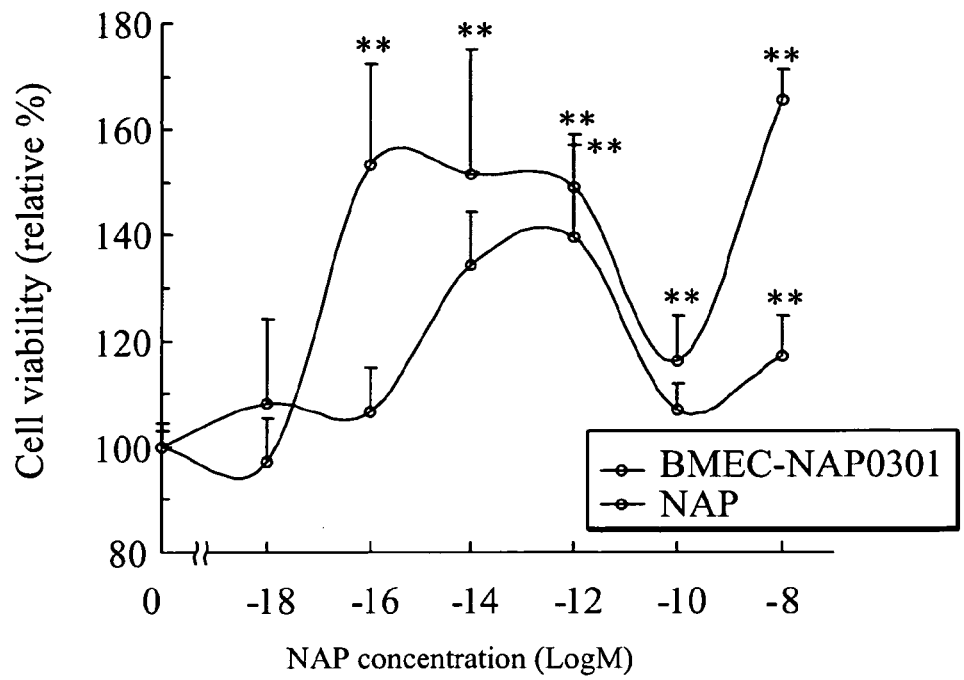
FIGS. 5A and 5B are diagrams showing the neural protection of BMEC-NAP03 series of the embodiments of the NAP derivatives.
Figure 5B:
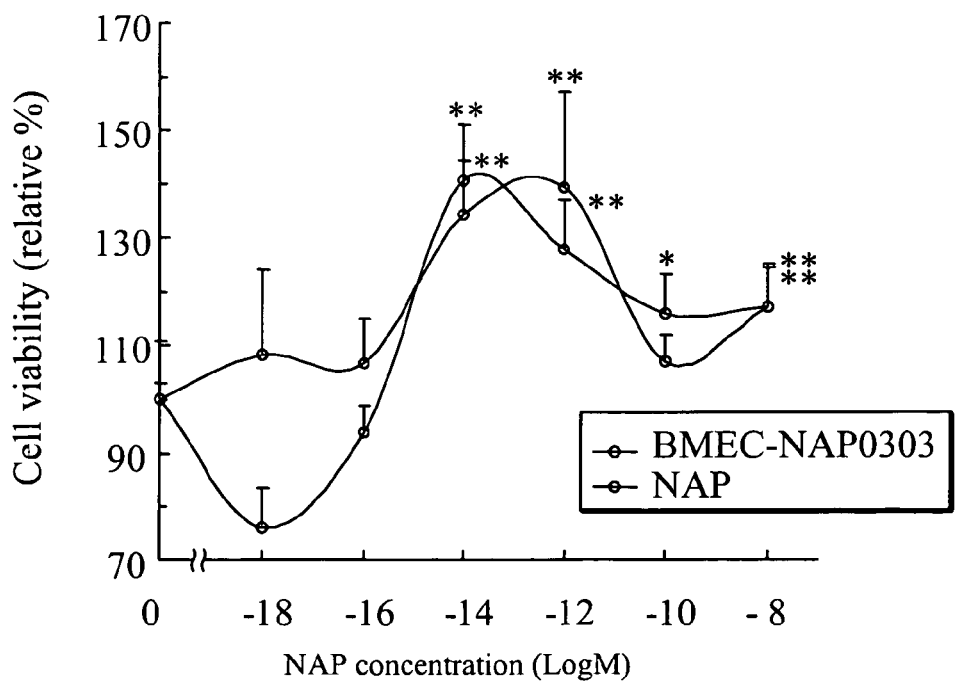
Figure 6A:
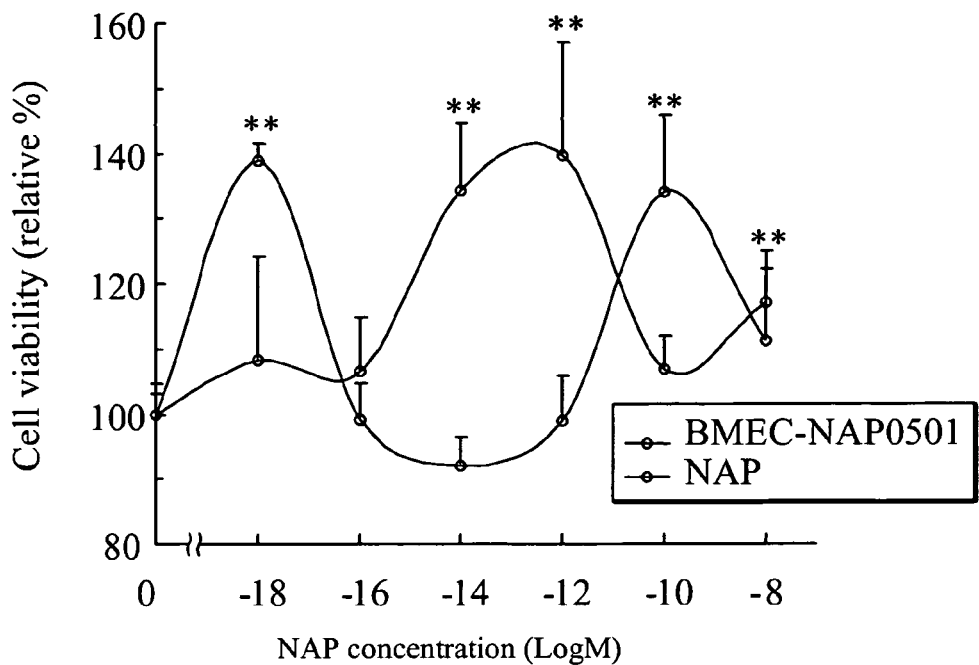
FIGS. 6A to 6D are diagrams showing the neural protection of BMEC-NAP05 series of the embodiments of the NAP derivatives.
Figure 6B:
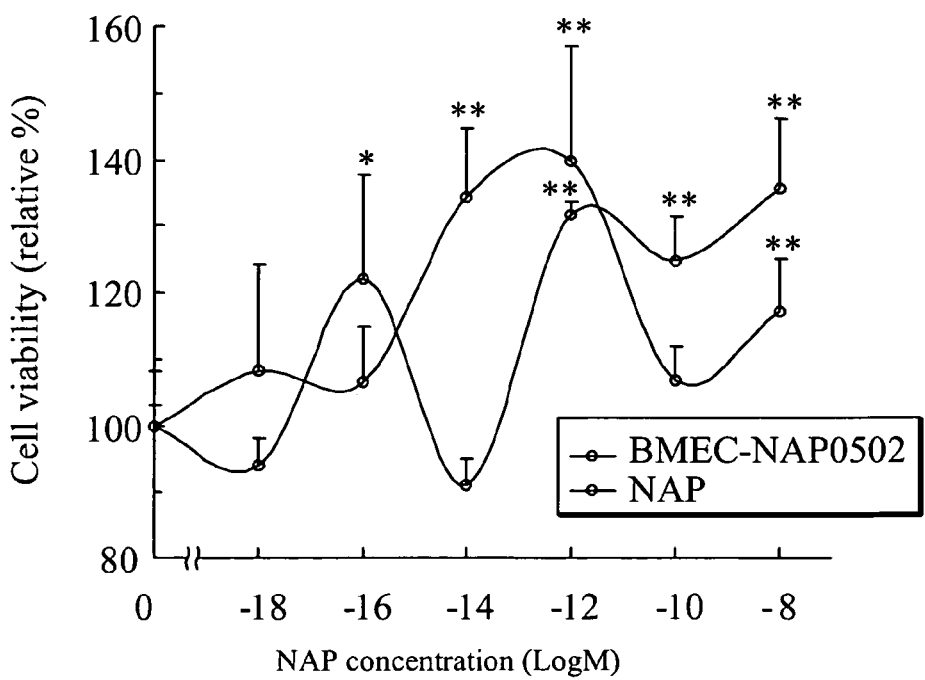
Figure 6C:
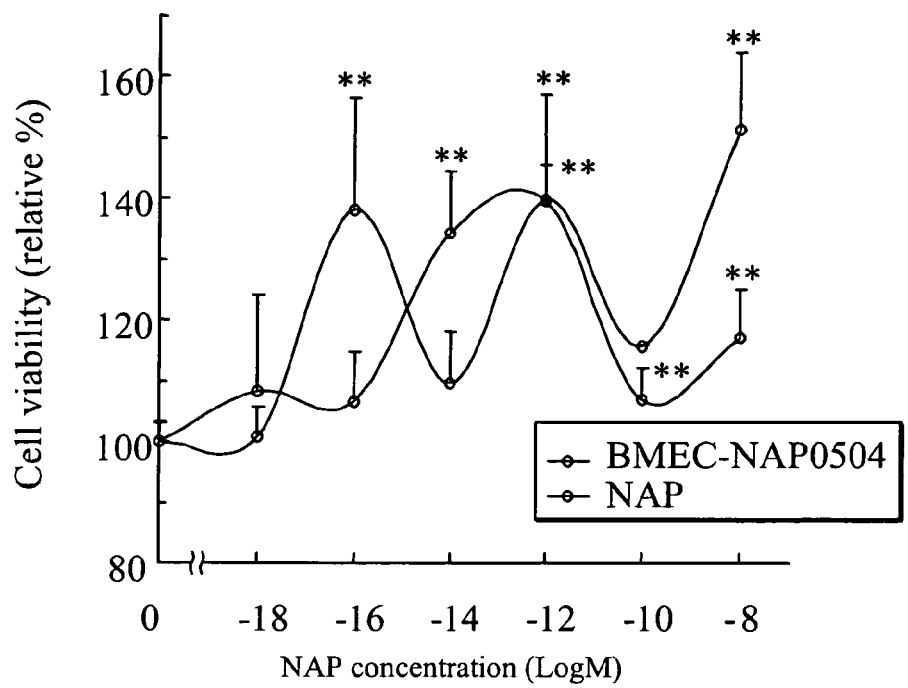
Figure 6D:
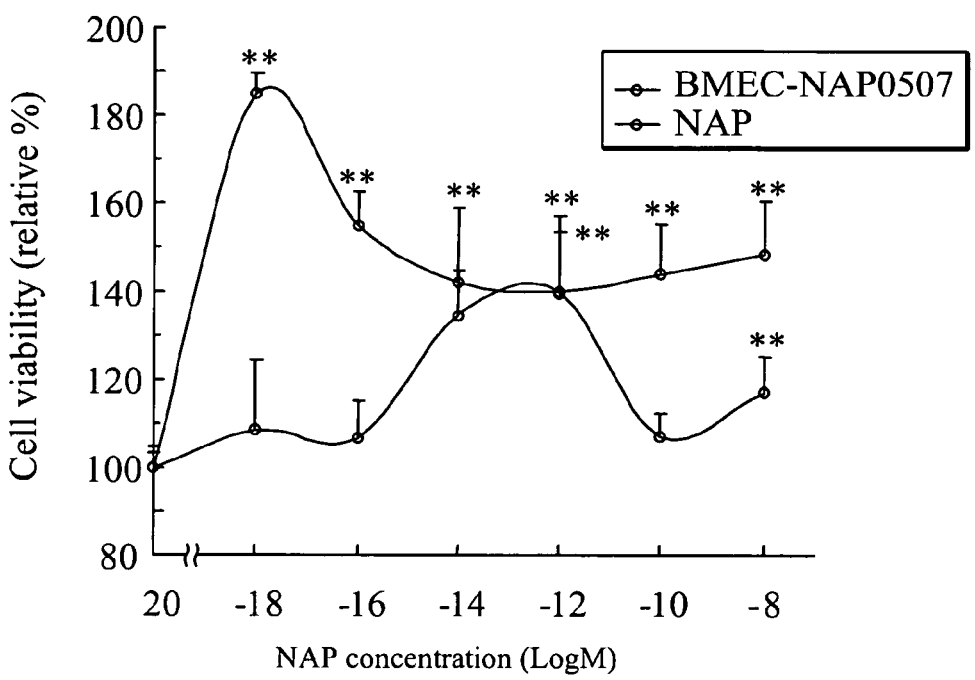
Figure 7A:
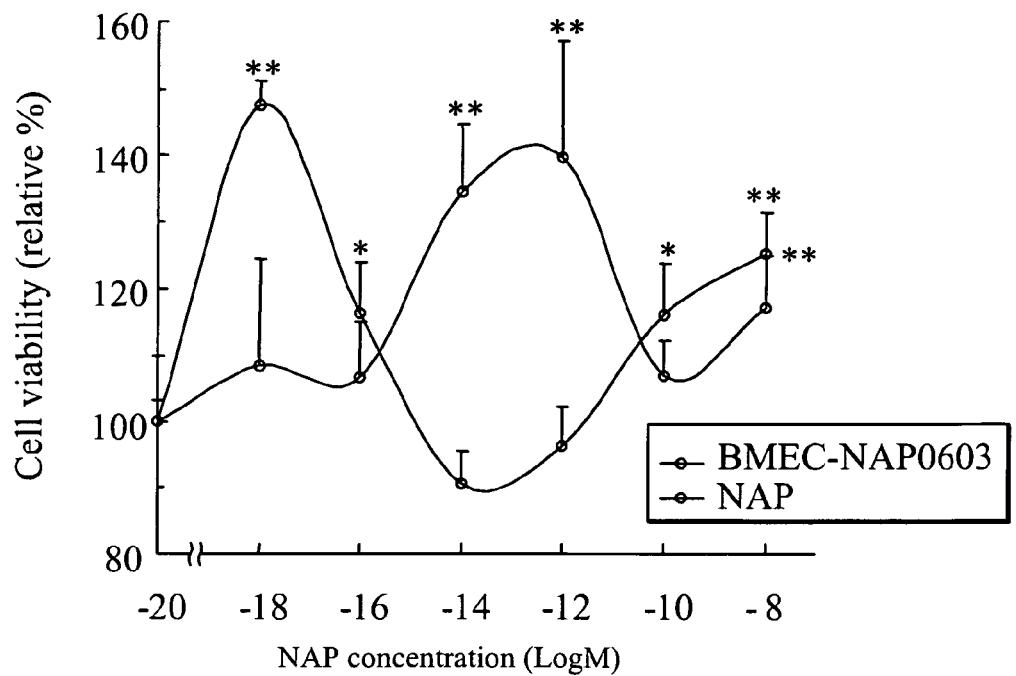
FIGS. 7A to 7D are diagrams showing the neural protection of BMEC-NAP06 series of the embodiments of the NAP derivatives.
Figure 7B:
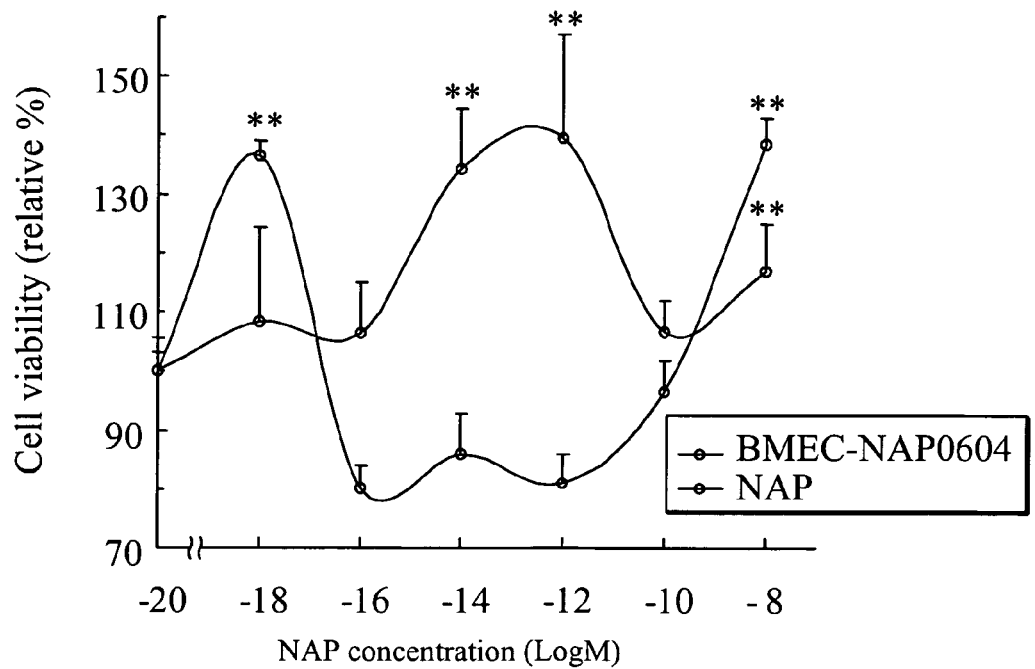
Figure 7C:
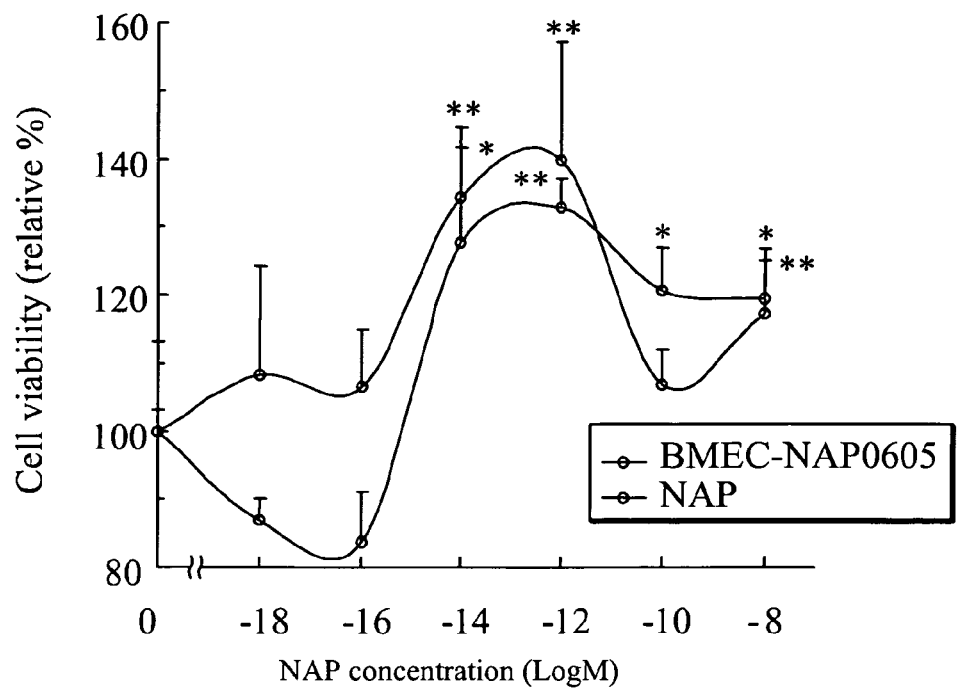
Figure 7D:
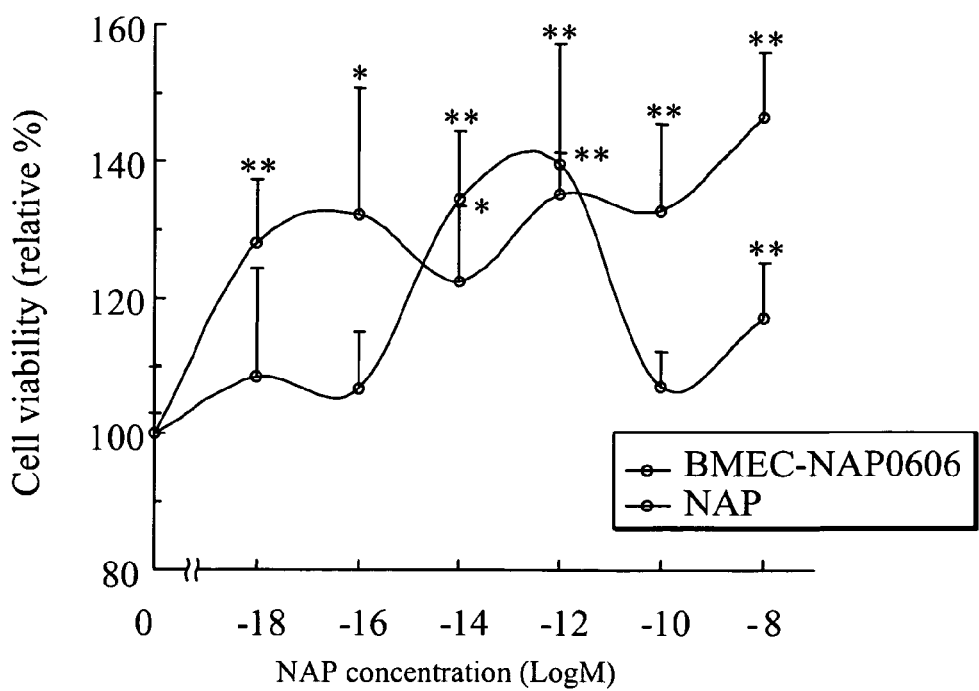
Figure 8A:
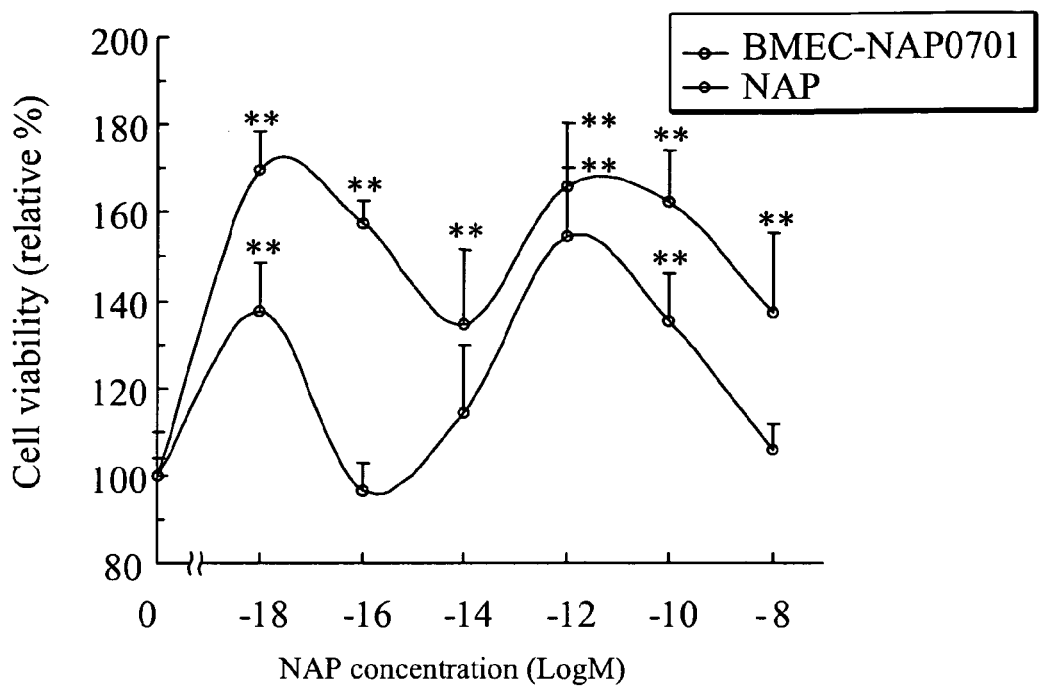
FIGS. 8A to 8D are diagrams showing the neural protection of BMEC-NAP07 series and BMEC-NAP08 series of the embodiments of the NAP derivatives.
Figure 8B:
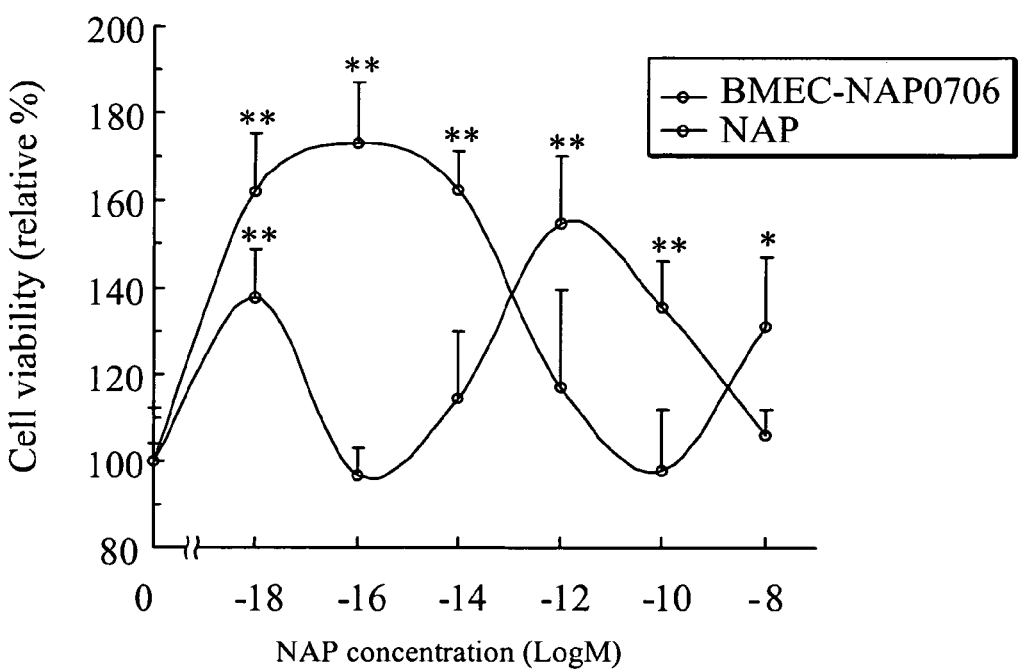
Figure 8C:
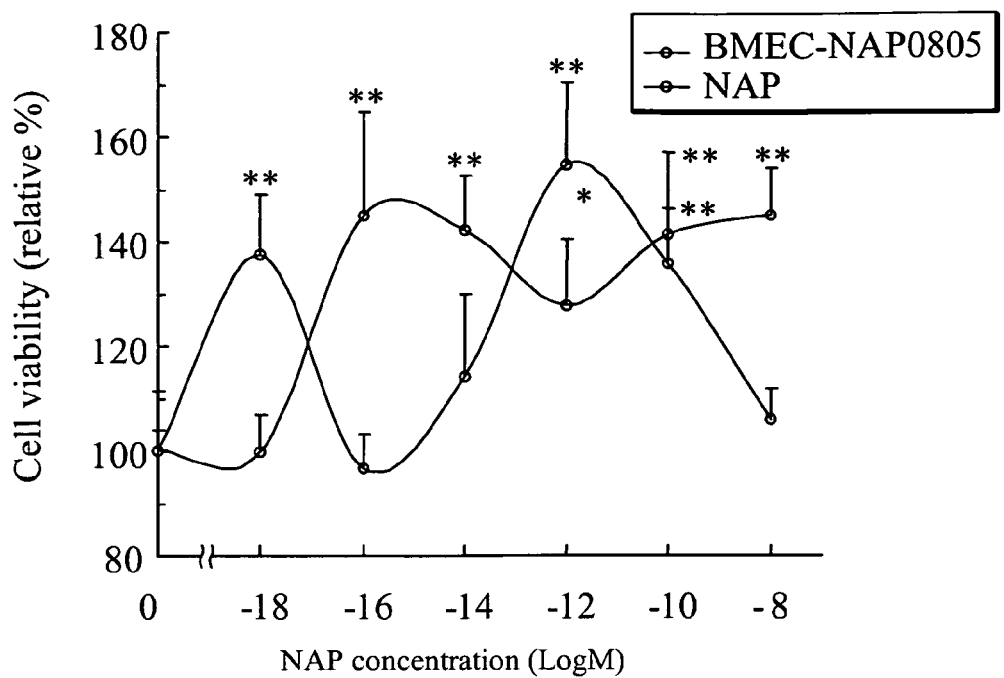
Figure 8D:
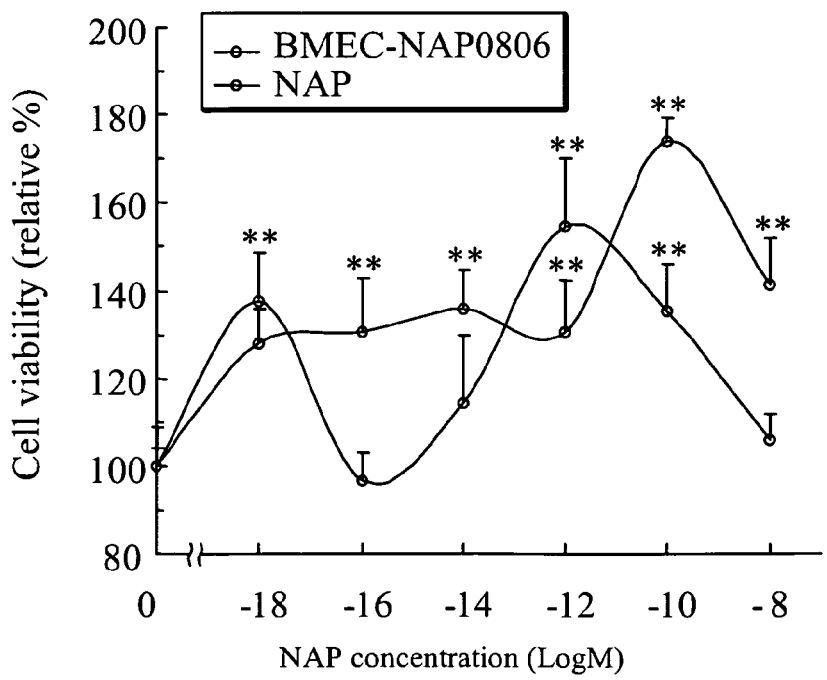

The neural protection of NAP and the NAP derivatives prepared in EXAMPLE 1 were measured by $H_2O_2$/PC12 cell system. PC12 cells ($4 \times 10^4$ cells) were seeded into a 96-well plate and incubated for 24 hours. NAP and the NAP derivatives prepared in EXAMPLE 1 at different concentration were added into the plate and incubated at 37° C. for 4 hours. Hydrogen peroxide with a concentration of 500 μM was then added to induce cytotoxicity. After 24 hours, supernatants were discarded and MTT [3-(4,5-dimethylthiazol-2-yl)-2,5-diphenyltetrazolium bromide] solution (0.5 mg/ml) was added for 4-hour reaction at 37° C. One hundred and fifty µl of DMSO was added to solve formazan product. Absorbance was measured by Microplate Reader at 570 nm, and cell viability was calculated. The results were shown in FIG. 2. In $H_2O_2$/PC12 cell system, NAP had cell protection effect at femtomolar (i.e. $10^{-15}$) level. Cell viability was increased at picomolar (i.e. $10^{-12}$) level. FIGS. 3 to 8 show the cell protection of the NAP derivatives from $H_2O_2$-induced PC12 cytotoxicity. FIGS. 3A to 3D show the results of the NAP derivatives of the BMEC-NAP01 series (BMEC-NAP0104, BMEC-NAP0105, BMEC-NAP0106, and BMEC-NAP0107); FIGS. 4A to 4D show the results of the NAP derivatives of the BMEC-NAP02 series (BMEC-NAP0201) and the BMEC-NAP04 series (BMEC-NAP0401, BMEC-NAP0404, and BMEC-NAP0407); FIGS. 5A and 5B show the results of the BMEC-NAP03 series (BMEC-NAP0301 and BMEC-NAP0303); FIGS. 6A to 6D shows the results of the BMEC-NAP05 series (BMEC-NAP0501, BMEC-NAP0502, BMEC-NAP0504, and BMEC-NAP0507); FIGS. 7A to 7D show the results of the BMEC-NAP06 series (BMEC-NAP0603, BMEC-NAP0604, BMEC-NAP0605, and BMEC-NAP0606); FIGS. 8A to 8D show the results of the BMEC-NAP07 series (BMEC-NAP0701 and BMEC-NAP0706) and the BMEC-NAP08 series (BMEC-NAP0805 and BMEC-NAP0806). The results show that some NAP derivatives have similar cell protection as NAP at femtomolar level. In addition, some NAP derivatives have superior cell protection than NAP and exhibit cell protection at 1/1000 of femtomolar level, i.e. $10^{-18}$ molar level.

Example 5

Pharmacokinetics of the NAP Derivatives

A single dosage of NAP and the NAP derivative of BMEC-NAP0706 were subcutaneously administered to rats respectively, and blood samples were obtained at different time intervals. The blood samples were subjected to LC-MS/MS analysis to measure the concentration of NAP and the NAP derivative. A time-plasma concentration relationship was established and pharmacokinetic parameters were calculated. The procedures are described below.

Long Evans rats with body weight between 220 to 240 g were obtained from the National Laboratory Animal Center, Taiwan and caged in the laboratory animal housing in the Industrial Technology Research Institute, Taiwan. The Breeding procedure follows the "Guide for the Care and Use of Laboratory Animals" established by the Chinese Society of Laboratory Animal Sciences. The rats were kept on an alternating 12-hour light and 12-hour dark schedule with sufficient feed and water until they reached the body weight between 280 to 300 g.

Each rat was weighed before the pharmacokinetic examination to estimate its own dosage. The tested drug dissolved in PBS was formulated to achieve the amount of one dosage between 0.28 to 0.32 mL. Each rat was subcutaneously administered with 1 mg/kg of the tested drug. 0.3 mL of blood samples were collected from the saphenous vein in medial thigh of the rat before and 0.25-, 0.5-, 0.75-, 1-, 2-, 4-, 24-hour after administration. Whole blood was centrifuged under 3500 rpm for 10 min and supernatant (serum) was moved to a clean 1.5 mL eppendorf and stored at −80° C.

Sample pretreatment was as follows: The frozen serum was thawed in an ice bath. One hundred µL of the serum was moved to a clean 1.5 mL eppendorf and 10 µL of internal standard material was added. The mixture was added with 200 µL ACN and mixed again. The sample was centrifuged under 14000 rpm at 4° C. for 10 min, and the supernatant was moved to the other clean eppendorf and dried in a vacuum system at 60° C. for 30 min. The dried sample was dissolved in 900 µL dd$H_2O$. The sample was added to a solid phase extraction column previously activated with methanol and dd$H_2O$. After the sample passed through, the extraction column was washed with dd$H_2O$ alone and then dd$H_2O$ containing 5% ACN and 0.1% TFA. The sample was dissolved from the extraction column with ACN containing 0.1% TFA and dried under a vacuum system at 60° C. for 1 hour. The dried sample was redissolved with 100 µL of dd$H_2O$ containing 50% ACN. The sample was analyzed with HPLC-MS/MS system.

The sample analysis was as described below. 20 µL of the sample was poured into the HPLC-MS/MS system. The solvent system was applied in gradient partitioning: 90% A ($H_2O$/ACN=98/2, 0.1% F.A.) and 10% B ($H_2O$/ACN=20/80, 0.1% F.A.) at 0-3 min; 10% A and 90% B at 3-6.5 min; 90% A and 10% B again at 6.5-15 min. The flow rate was 0.2 mL/min. The column was ZORBAX C18, 5 µm, 2.1×50 mm (Agilent) and the detector was ABI 4000 Q Trap. Each sample was analyzed for 15 min. The results were compared with the standard calibration curve to estimate the concentration of each sample. All data was statistically analyzed with Excel or WinNonlin.

Figure 9A:
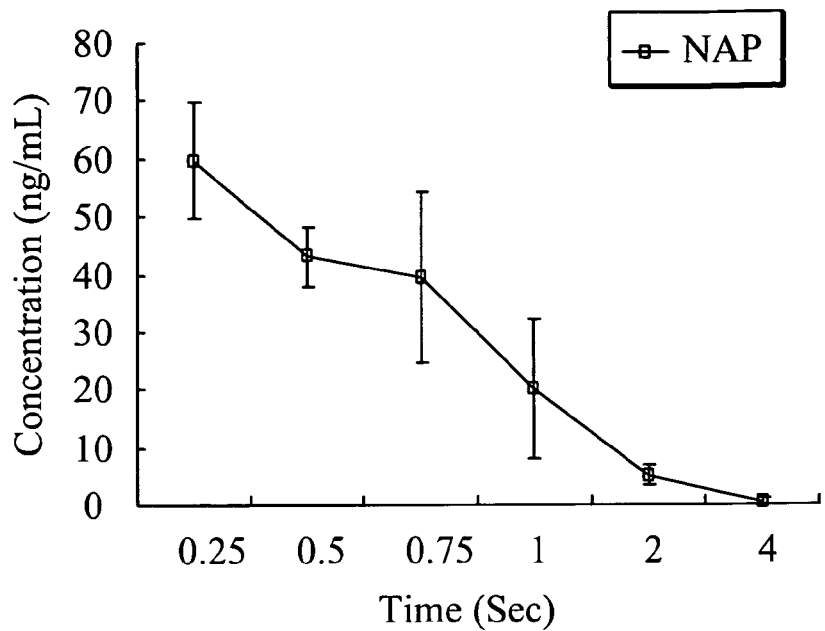
FIGS. 9A and 9B are diagrams showing the pharmacokinetic features of NAP and the embodiments of the NAP derivatives in the invention.
Figure 9B:
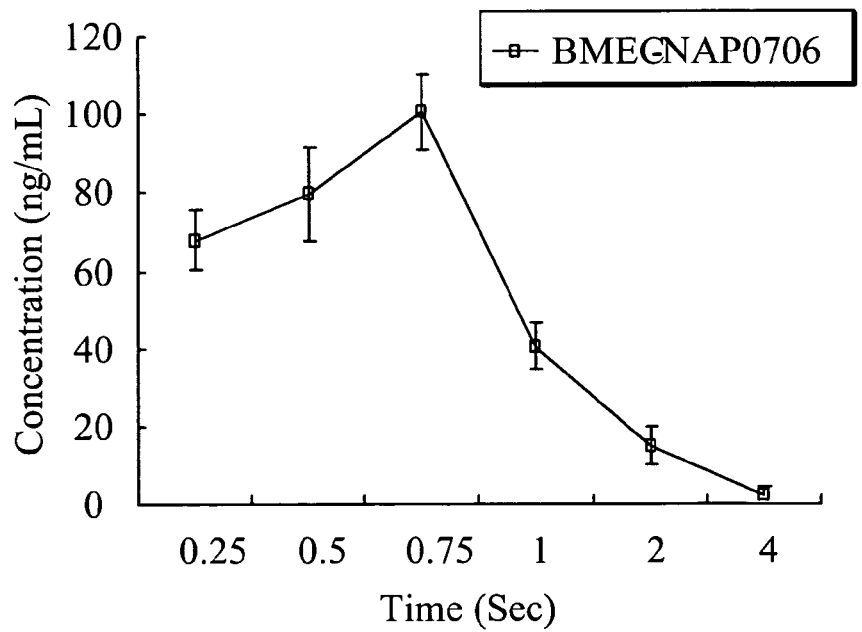

FIGS. 9A and 9B show the time to plasma concentration relationship of NAP and the NAP derivative of BMEC-NAP0706, indicating the NAP derivative BMEC-NAP0706 has superior pharmacokinetic property than NAP. The pharmacokinetic parameters comparison of the NAP derivative BMEC-NAP0706 and NAP was listed in Table 4. AUC of BMEC-NAP0706 was twice that of NAP, indicating the target organ or tissue in the living organism has a higher exposure to the drug. The half-life of BMEC-NAP0706 is longer than that of NAP, indicating the drug has a longer acting time in vivo and the administration interval can be prolonged; The maximum plasma concentration of BMEC-NAP0706 is twice that of NAP, indicating the NAP derivative has stronger effects. BMEC-NAP0706 has a longer Tmax than NAP, however, the time required to reach the highest concentration of BMEC-NAP0706 and NAP is 0.25 hours, indicating the NAP derivative has similar effective time as NAP.

TABLE 4

Pharmacokinetic parameters of the NAP derivative BMEC-NAP0706 and NAP

| | BMEC-NAP0706 | NAP |
|---|---|---|
| AUC (h * ng/mL) | 103.80 | 55.75 |
| T½ (h) | 0.91 | 0.85 |
| Cmax (ng/ml) | 100.77 | 55.5 |
| Tmax (h) | 0.75 | 0.25 |
| TNAP-max (h) | 0.25 | 0.25 |

Example 6

Animal Activity Test

Scopolamine-induced amnesia mice were used in combination of Morris water maze, a memory and behavior analysis system, to assess the in vivo effects of the NAP derivative BMEC-NAP0701 and NAP.

Sprague-Dawley male rats with body weight of 220-250 g obtained from the National Laboratory Animal Center, Taiwan, were caged in an air-conditioned housing with a temperature of 23±1° C. and kept on an alternating 12-hour light and 12-hour dark schedule with sufficient feed and water.

The amnesia animal model was established by the induction of scopolamine which is a cholinergic muscarinic receptor antagonist and blocks the signal transmittion mediated by acetylcholine in the brain to produce learning disorder. The effects of scopolamine are reversible and do not cause permanent damage of memory. Administration of scopolamine was preformed by intraperitoneal injection with a dosage of 1 mg/kg. Five minutes after the administration, the rats were subcutaneously injected with NAP or the NAP derivative of BMEC-NAP0701 in a dosage of 0.25 mg/kg. The treated rats were subjected to Morris water maze after 25 minutes.

Figure 10:
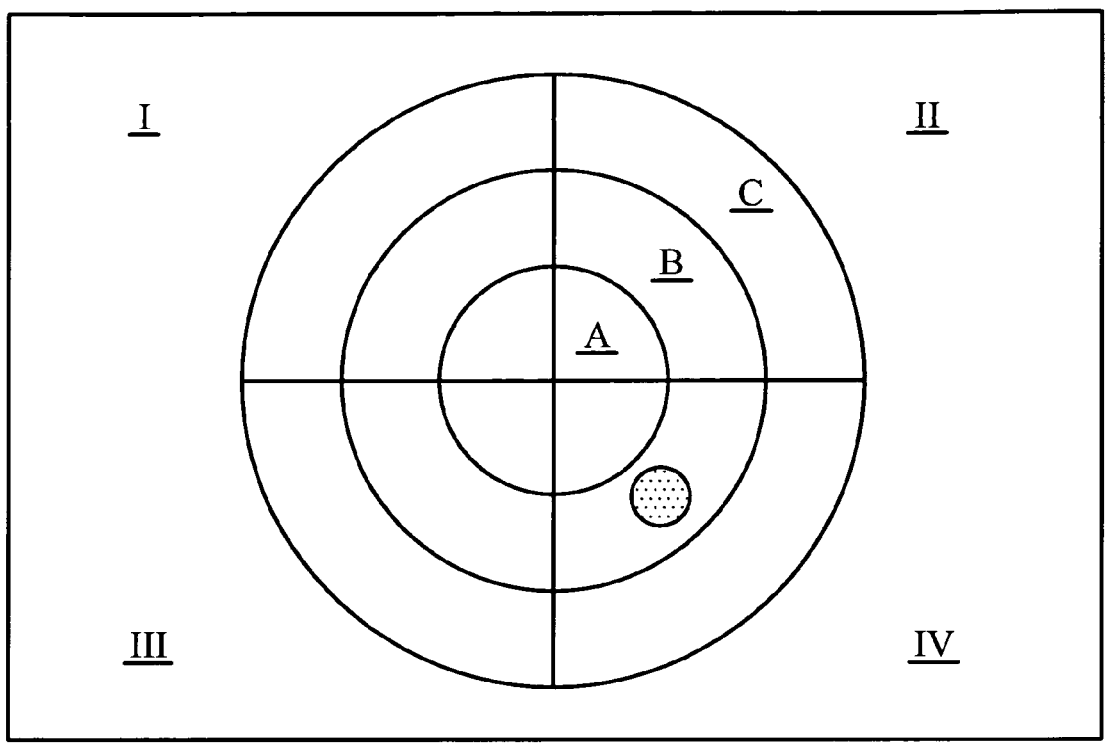
FIG. 10 is a diagram showing the location of the swimming pool and target area (platform) in the water maze test of Example 6.

Morris Water Maze was performed with a water maze device containing a stainless pool with a size of 160 cm in diameter, 50 cm in height, and 15 mm in thickness of the wall and a platform with a size of 11 cm in diameter, and 22 cm in height. When the pool was filled with water, the platform was submerged 1 cm beneath water level. The water temperature was controlled at 23±1° C. As shown in FIG. 10, the pool was divided into four quadrants (I, II, III, and V) and three concentric circles (from the center of the circle, each are circle A, B, and C), and the platform was located in quadrant IV about 1 cm beneath the surface of water. The swimming time and track were recorded by VEDEOMEX-V video tracing system, video recorder, and monitor (Columbus Instruments) and analyzed by Water Maze Program (Columbus Instruments).

The learning and memory test was performed by Morris Water Maze as described below.

The first day to early on the third day: The water pool was divided into four quadrants and the platform was located at zone B of quadrant IV. The rats were sequentially sent to the four quadrants, trained four times a day, 2 minutes each time. If the rat found the platform in 2 min, the rat was allowed to rest in the platform for 30 seconds, and the rat was moved out of the pool to have a 30-minute rest. The total training time is three days and this stage is the "learning stage".

Late of the third day: Two to four hours after the third day training, the platform was removed from the pool. The trained rats were separately sent to quadrant I and the swimming track was recorded for 60 sec. The time spent in finding the original platform was also recorded. This stage is the "reference memory stage".

The fourth day: The platform was placed in the quadrant IV and lifted above water level about 1 cm. The rats were trained four times. This stage is the "non-spatial memory stage.

Early of the fifth day: The platform was placed in the quadrant II and submerged beneath water level about 1 cm. The rats were separately sent to quadrant I and the time spent in finding the platform was recorded. This stage is the "reacquisition stage".

Late on the fifth day: Two to four hours after the early training, the rats were separately sent to quadrant III and the time spent in finding the platform was recorded. This stage is "retrieval stage". The swimming tracks of all rats were recorded. The training stages early and late on the fifth day can be referred to the "working memory stage".

The results of the "reference memory stage" and the "working memory stage" were analyzed. Independent sample T test was applied to analyze the statistical significance. P value <0.05 indicates the result has statistical significance. The memory improvement of the drug was estimated by the results.

Figure 11:
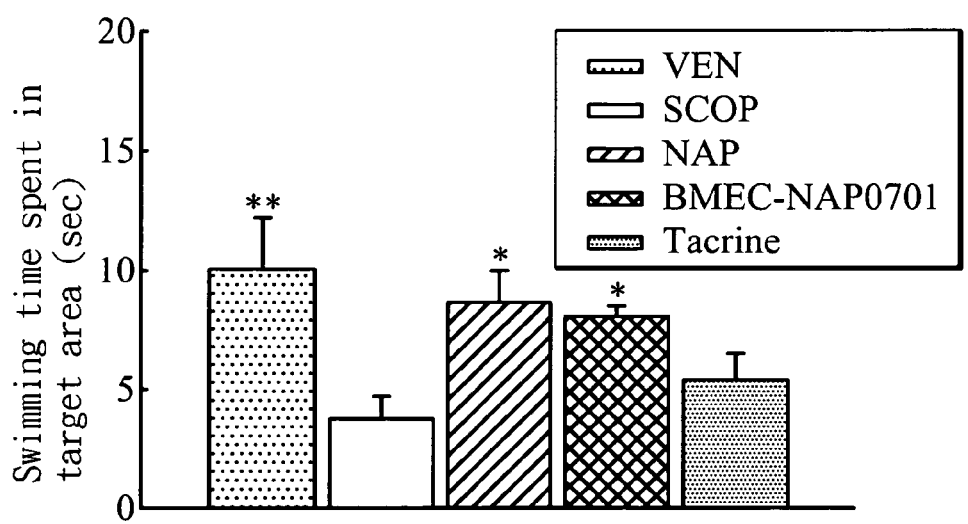
FIG. 11 is a diagram showing the effect of the embodiments of the NAP derivative in the invention to the scopolamine-induced amnesia rats. VEH is the vehicle group; SCOP is the scopolamine-induced group; NAP is the scopolamine-induced and NAP-treated group BMEC-NAP0701 is the scopolamine-induced and BMEC-NAP0701-treated group; Tacrine is the scopolamine-induced and tacrine-treated group.

The results were shown in FIG. 11. The differences of the time spent in finding the platform for Scopolamine-induced rats and vehicle-treated rats have statistical significance. The time differences of the scopolamine-induced, NAP-treated rats and the scopolamine-induced rats also have statistical significance, indicating NAP has memory improving effect in vivo. The time differences of the scopolamine-induced, BMEC-NAP0701-treated rats or the scopolamine-induced, NAP-treated rats, and the scopolamine-induced rats have statistical significance, however, the time differences of the BMEC-NAP0701-treated rats or NAP-treated rats have no statistical significance, indicating the NAP derivative of BMEC-NAP0701 has memory improving effect similar to NAP in vivo. Tacrine used to treat the symptoms of Alzheimer's disease was applied as reference.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An oligopeptide having the formula of:

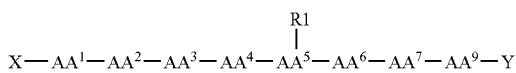

(I)

wherein
each $AA^1$ and $AA^9$ is independently Asn or Gln;
each $AA^2$ and $AA^8$ is independently Ala, or Gly;
each $AA^3$ and $AA^7$ is independently Pro or homoproline (pipeconic acid);
each $AA^4$ and $AA^6$ is independently Val, Leu, or Ile;
$AA^5$ is Ser or Thr;
$R^1$ is hydrogen, phosphate, phosphate ester, sulfate, sulfate ester, or salt derivatives thereof;
X links to nitrogen of $AA^1$ and is $-COR^2$, $-COOR^3$, $-SO^2R^4$; wherein $R^2$ and $R^3$ are each independently or together substituted or unsubstituted $C_{6-18}$ aryl, or substituted or unsubstituted $C_{1-12}$ heteroaryl; and $R^4$ is substituted or unsubstituted $C_{1-32}$ alkyl, substituted or unsubstituted $C_{2-32}$ alkenyl, substituted or unsubstituted $C_{2-32}$ alkynyl, substituted or unsubstituted $C_{6-18}$ aryl, or substituted or unsubstituted $C_{1-12}$ heteroaryl; and
Y links to carbonyl group of $AA^9$ and is $-OR^5$, or $-NR^6R^7$; $R^5$, $R^6$, $R^7$ are each independently or together hydrogen, substituted or unsubstituted $C_{1-32}$ alkyl, substituted or unsubstituted $C_{2-32}$ alkenyl, substituted or unsubstituted $C_{2-32}$ alkynyl, substituted or unsubstituted $C_{6-18}$ aryl, or substituted or unsubstituted $C_{1-12}$ heteroaryl.

2. The oligopeptide of claim 1, wherein $AA^2$ is Ala.

3. The oligopeptide of claim 1, wherein $AA^8$ is Ala.

4. The oligopeptide of claim 1, wherein $R^1$ is hydrogen or phosphate.

5. The oligopeptide of claim 1, wherein
   X is selected from the group consisting of benzoyl, α-napthoyl, 4-phenylbenzoyl, 2-thiophenecarbonyl, bezyloxycarbonyl (Cbz), and fluorenylmethyloxycarbonyl (Fmoc);
   Y is —OH; and
   $R^1$ is hydrogen.

6. The oligopeptide of claim 5, wherein X is selected from the group consisting of benzoyl and fluorenylmethyloxycarbonyl (Fmoc).

7. The oligopeptide of claim 1, wherein
   X is selected from the group consisting of benzoyl, α-napthoyl, 4-phenylbenzoyl, 2-thiophenecarbonyl, bezyloxycarbonyl (Cbz), and fluorenylmethyloxycarbonyl (Fmoc);
   Y is —$NH_2$; and
   $R^1$ is hydrogen.

8. The oligopeptide of claim 7, wherein X is selected from the group consisting of bezyloxycarbonyl (Cbz), and fluorenylmethyloxycarbonyl (Fmoc).

9. The oligopeptide of claim 1, wherein
   X is fluorescein-5(6)-carbonyl 5(6)-FAM);
   Y is —OH; and
   $R^1$ is hydrogen.

10. An oligopeptide
    selected from the group consisting of NAPVSIPAQ (SEQ ID NO: 6), QAPVSIPO (SEQ ID NO: 7), and NAPVSIPN (SEQ ID NO: 8).

11. The oligopeptide of claim 10, wherein the oligopeptide is NAPVSIPN (SEQ ID NO: 8).

12. A pharmaceutical composition, comprising the oligopeptide of claim 1.

* * * * *

UNITED STATES PATENT AND TRADEMARK OFFICE
CERTIFICATE OF CORRECTION

PATENT NO. : 7,544,666 B2  Page 1 of 1
APPLICATION NO. : 11/440174
DATED : June 9, 2009
INVENTOR(S) : On Lee et al.

It is certified that error appears in the above-identified patent and that said Letters Patent is hereby corrected as shown below:

In Claim 1, Formula (I), beginning on line 5:

""

should read:

-- 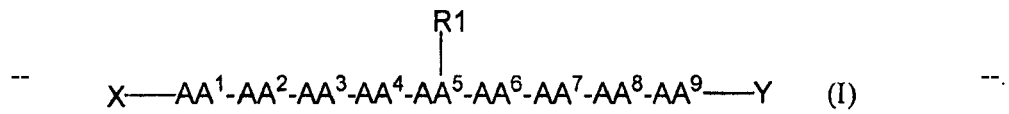 --.

Signed and Sealed this

First Day of June, 2010

David J. Kappos
*Director of the United States Patent and Trademark Office*

SEQUENCE LISTING

```
<160> NUMBER OF SEQ ID NOS: 17

<210> SEQ ID NO 1
<211> LENGTH: 14
<212> TYPE: PRT
<213> ORGANISM: Homo sapiens

<400> SEQUENCE: 1

Val Leu Gly Gly Gly Ser Ala Leu Leu Arg Ser Ile Pro Ala
1               5                   10

<210> SEQ ID NO 2
<211> LENGTH: 9
<212> TYPE: PRT
<213> ORGANISM: Homo sapiens

<400> SEQUENCE: 2
```

-continued

```
Ser Ala Leu Leu Arg Ser Ile Pro Ala
1               5

<210> SEQ ID NO 3
<211> LENGTH: 8
<212> TYPE: PRT
<213> ORGANISM: Homo sapiens

<400> SEQUENCE: 3

Asn Ala Pro Val Ser Ile Pro Gln
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence:
      Synthetically modified oligopeptide
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (5)..(5)
<223> OTHER INFORMATION: Xaa can be any amino acid
<220> FEATURE:
<221> NAME/KEY: misc_feature
<222> LOCATION: (7)..(8)
<223> OTHER INFORMATION: Xaa can be any amino acid

<400> SEQUENCE: 4

Asn Xaa Xaa Val Xaa Ile Xaa Xaa Gln
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:
      Synthetically modified oligopeptide
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (5)..(5)
<223> OTHER INFORMATION: Xaa can be any amino acid
<220> FEATURE:
<221> NAME/KEY: misc_feature
<222> LOCATION: (7)..(8)
<223> OTHER INFORMATION: Xaa can be any amino acid

<400> SEQUENCE: 5

Gln Xaa Xaa Val Xaa Ile Xaa Xaa Asn
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence:
      Synthetically modified oligopeptide

<400> SEQUENCE: 6

Asn Ala Pro Val Ser Ile Pro Ala Gln
```

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence:
      Synthetically modified oligopeptide

<400> SEQUENCE: 7

Gln Ala Pro Val Ser Ile Pro Gln
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence:
      Synthetically modified oligopeptide

<400> SEQUENCE: 8

Asn Ala Pro Val Ser Ile Pro Asn
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence:
      Synthetically modified oligopeptide

<400> SEQUENCE: 9

Asn Ala Pro Ile Ser Ile Pro Gln
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence:
      Synthetically modified oligopeptide

<400> SEQUENCE: 10

Asn Ala Pro Val Ser Val Pro Gln
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence:
      Synthetically modified oligopeptide

<400> SEQUENCE: 11

Asn Ala Pro Val Ser Leu Pro Gln
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence:

-continued

Synthetically modified oligopeptide

<400> SEQUENCE: 12

Gln Ala Pro Val Ser Val Pro Ala Gln
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence:
      Synthetically modified oligopeptide

<400> SEQUENCE: 13

Asn Ala Pro Ile Ser Ile Pro Ala Asn
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence:
      Synthetically modified oligopeptide

<400> SEQUENCE: 14

Asn Ala Pro Val Ser Ile Pro Asn
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence:
      Synthetically modified oligopeptide

<400> SEQUENCE: 15

Asn Ala Pro Ile Ser Ile Pro Gln
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence:
      Synthetically modified oligopeptide

<400> SEQUENCE: 16

Asn Ala Pro Val Ser Val Pro Gln
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence:
      Synthetically modified oligopeptide

<400> SEQUENCE: 17

Asn Ala Pro Val Ser Leu Pro Gln
1               5